US012564590B2

(12) United States Patent
McGeehan et al.

(10) Patent No.: US 12,564,590 B2
(45) Date of Patent: Mar. 3, 2026

(54) COMBINATIONS OF MENIN INHIBITORS AND CYP3A4 INHIBITORS AND METHODS OF USE THEREOF

(71) Applicant: Syndax Pharmaceuticals, Inc., Waltham, MA (US)

(72) Inventors: Gerard M. McGeehan, Newtown Square, PA (US); Peter Ordentlich, Lexington, MA (US); Galit Rosen, Newton, MA (US); Steven A. Smith, San Jose, CA (US)

(73) Assignee: Syndax Pharmaceuticals, Inc., New York, NY (US)

( * ) Notice: Subject to any disclaimer, the term of this patent is extended or adjusted under 35 U.S.C. 154(b) by 620 days.

(21) Appl. No.: 17/917,193

(22) PCT Filed: Apr. 7, 2021

(86) PCT No.: PCT/US2021/026141

§ 371 (c)(1),
(2) Date: Oct. 5, 2022

(87) PCT Pub. No.: WO2021/207335

PCT Pub. Date: Oct. 14, 2021

(65) Prior Publication Data

US 2023/0165858 A1 Jun. 1, 2023

Related U.S. Application Data

(60) Provisional application No. 63/006,574, filed on Apr. 7, 2020.

(51) Int. Cl.

| | |
|---|---|
| ***A61K 31/506*** | (2006.01) |
| ***A61K 31/496*** | (2006.01) |
| ***A61P 35/00*** | (2006.01) |

(52) U.S. Cl.

CPC .......... *A61K 31/506* (2013.01); *A61K 31/496* (2013.01); *A61P 35/00* (2018.01)

(58) Field of Classification Search

CPC .............. A61K 2300/00; A61K 31/496; A61K 31/506; A61K 31/513; A61K 45/06; A61P 35/00; A61P 35/02

See application file for complete search history.

(56) References Cited

U.S. PATENT DOCUMENTS

| | | | |
|---|---|---|---|
| 5,292,740 | A | 3/1994 | Burri et al. |
| 5,820,915 | A | 10/1998 | Harris |
| 5,990,154 | A | 11/1999 | Harris |
| 5,993,887 | A | 11/1999 | Harris |
| 6,054,477 | A | 4/2000 | Harris |
| 6,063,809 | A | 5/2000 | Harris |
| 6,124,477 | A | 9/2000 | Harris |
| 6,162,479 | A | 12/2000 | Harris |
| 6,248,776 | B1 | 6/2001 | Harris |
| 6,255,337 | B1 | 7/2001 | Harris |
| 6,309,687 | B1 | 10/2001 | Harris |
| 6,476,066 | B1 | 11/2002 | Harris |
| 6,660,766 | B2 | 12/2003 | Harris |

(Continued)

FOREIGN PATENT DOCUMENTS

| | | | |
|---|---|---|---|
| CN | 105732636 | A | 7/2016 |
| JP | 2014517016 | A | 7/2014 |

(Continued)

OTHER PUBLICATIONS

Cecil Textbook of Medicine, 20th Ed., vol. 1 (Year: 1997).*
Wu et al., Small-molecule inhibitors, immune checkpoint inhibitors, and more: FDA-approved novel therapeutic drugs for solid tumors from 1991 to 2021; Journal of Hematology & Oncology, 15, 143 (Year: 2022).*
Pounds et al., "Repurposing itraconazole for the treatment of cancer (Review)", Oncology Letters, 2587-2597 (Year: 2017).*
Baell et al., "Inhibitors of histone acetyltransferases KAT6A/B induce senescence and arrest tumour growth," Nature 560(7717):253-257 (2018).
CAS Registry No. 180-43-8; Spiro[5.5]undecane, STN Entry Date: Nov. 16, 1984; 1 page.
CAS Registry No. 236406-49-8; Tert-butyl 2,7-diazaspiro [4.4]nonane-2-carboxylate, STN Entry Date: Sep. 1, 1999; 3 pages.

(Continued)

*Primary Examiner* — Jeffrey H Murray
*Assistant Examiner* — Daniel John Burkett
(74) *Attorney, Agent, or Firm* — Fenwick & West LLP; Heidi A. Erlacher; Eric A. Owens

(57) ABSTRACT

The present invention is directed to combinations of menin inhibitors with one or more CYP3A4 inhibitors, pharmaceutical compositions thereof, and methods of treating cancer and other diseases mediated by the menin-HLL interaction. Accordingly, the present disclosure provides compounds, e.g., of Formula (II), which inhibit menin and are useful in the treatment of diseases mediated by the menin-MLL interaction Formula (II)

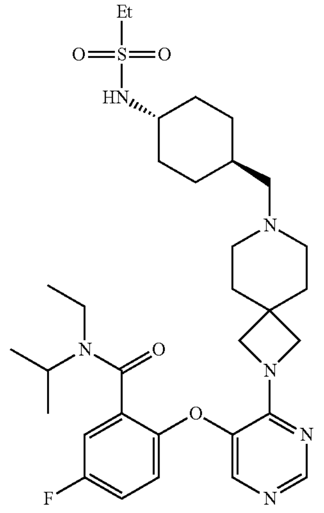

in combination with a strong CYP3A4 inhibitor.

32 Claims, 1 Drawing Sheet

(56) References Cited

U.S. PATENT DOCUMENTS

| | | | |
|---|---|---|---|
| 9,101,622 | B2 | 8/2015 | Zeldis |
| 9,969,727 | B2 | 5/2018 | Le et al. |
| 10,683,302 | B2 | 6/2020 | Cacatian et al. |
| 10,752,639 | B2 | 8/2020 | Wu et al. |
| 10,869,868 | B2 | 12/2020 | Armstrong |
| 11,479,557 | B2 | 10/2022 | Cacatian et al. |
| 12,312,359 | B2 | 5/2025 | Cacatian et al. |
| 2004/0058982 | A1 | 3/2004 | Harris |
| 2005/0209301 | A1 | 9/2005 | Eissenstat et al. |
| 2005/0267074 | A1 | 12/2005 | Eissenstat et al. |
| 2013/0102525 | A1 | 4/2013 | Bernstein et al. |
| 2014/0309427 | A1 | 10/2014 | Dutta |
| 2015/0329535 | A1 | 11/2015 | Sole Feu et al. |
| 2016/0339035 | A1 | 11/2016 | Berger et al. |
| 2018/0125839 | A1 | 5/2018 | Jain |
| 2018/0243303 | A1 | 8/2018 | Grembecka et al. |
| 2019/0076540 | A1 | 3/2019 | Phillips et al. |
| 2019/0144459 | A1 | 5/2019 | Cacatian et al. |
| 2019/0307750 | A1 | 10/2019 | Armstrong |
| 2020/0223853 | A1 | 7/2020 | Butler et al. |
| 2021/0115018 | A1 | 4/2021 | Wang et al. |
| 2021/0317214 | A1 | 10/2021 | Chartash et al. |
| 2024/0238291 | A1 | 7/2024 | Mcgeehan et al. |
| 2024/0400564 | A1 | 12/2024 | Cacatian et al. |
| 2025/0041299 | A1 | 2/2025 | Armstrong et al. |

FOREIGN PATENT DOCUMENTS

| | | | | |
|---|---|---|---|---|
| JP | 2018538330 | A | 12/2018 | |
| WO | WO-0054768 | A1 | 9/2000 | |
| WO | WO-2004037827 | A1 | 5/2004 | |
| WO | WO-2009137733 | A1 | 11/2009 | |
| WO | WO-2012170976 | A2 | 12/2012 | |
| WO | WO-2014164543 | A1 | 10/2014 | |
| WO | WO-2015191701 | A1 | 12/2015 | |
| WO | WO-2017112768 | A1 | 6/2017 | |
| WO | WO-2017192543 | A1 | 11/2017 | |
| WO | WO-2017214367 | A1 * | 12/2017 | ........... A61K 31/506 |
| WO | WO-2018053267 | A1 | 3/2018 | |
| WO | WO-2018175746 | A1 | 9/2018 | |
| WO | WO-2019120209 | A1 | 6/2019 | |
| WO | WO-2019143977 | A1 | 7/2019 | |
| WO | WO-2020069027 | A1 | 4/2020 | |
| WO | WO-2021207335 | A1 | 10/2021 | |
| WO | WO-2022241122 | A1 | 11/2022 | |
| WO | WO-2022241265 | A1 | 11/2022 | |
| WO | WO-2023018825 | A1 | 2/2023 | |
| WO | WO-2023114867 | A2 | 6/2023 | |
| WO | WO2025049521 | A1 | 3/2025 | |

OTHER PUBLICATIONS

Clinical Trial NCT02141828: A Phase 1 Dose Escalation and Expanded Cohort Study of EPZ-5676 in the Treatment of Pediatric Patients with Relapsed/Refractory Leukemias Bearing a Rearrangement of the MLL Gene, First Posted in 2014, 8 pages.

Clinical Trial NCT04065399: A Study of SNDX-5613 in R/R Leukemias Including Those With an MLL/KMT2A Gene Rearrangement or NPM1 Mutation (AUGMENT-101), First Posted in 2019, 8 pages.

Clinical Trial NCT04067336: First in Human Study of Ziftomenib in Relapsed or Refractory Acute Myeloid Leukemia, First Posted in 2019, 6 pages.

Clinical Trial NCT04606446: Study of PF-07248144 in Advanced or Metastatic Solid Tumors (KAT6), First Posted in 2020, 8 pages.

Clinical Trial NCT04752163: DS-1594b With or Without Azacitidine, Venetoclax, or Mini-HCVD for the Treatment of Relapsed or Refractory Acute Myeloid Leukemia or Acute Lymphoblastic Leukemia, First Posted in 2021, 16 pages.

Clinical Trial NCT04811560: A Study of JNJ-75276617 in Participants with Acute Leukemia, First Posted in 2021, 5 pages.

Clinical Trial NCT04988555: A Study of DSP-5336 in Relapsed/Refractory AML/ ALL With or Without MLL Rearrangement or NPM1 Mutation, First Posted in 2021, 7 pages.

Dafflon, C., et al.; "Complementary activities of DOT1L and Menin inhibitors in MLL-rearranged leukemia," Leukemia (2017); 31(6):1269-1277.

Daigle, S.R. et al. (2011) "Selective Killing of Mixed Lineage Leukemia Cells by a Potent Small-Molecule DOT1L Inhibitor" Cancer Cell, 20(1):53-65.

Dinardo C., et al., "Clinical experience with the BCL2-inhibitor venetoclax in combination therapy for relapsed and refractory acute myeloid leukemia and related myeloid malignancies," American journal of hematology, 2018, vol. 93(3), pp. 401-407.

Fiskus et al., "Effective Menin inhibitor-based combinations against AML with MLL rearrangement or NPM1 mutation (NPM1c)," Blood Cancer J. (2022); 12(1):5, 11 pages.

Godamudunage, M.P., et al.; "Comparison of Antifungal Azole Interactions with Adult Cytochrome P450 3A4 versus Neonatal Cytochrome P450 3A7," Drug Metab Dispos. (2018); 46(9):1329-1337.

Hemming, M.L., et al.; "Enhancer Domains in Gastrointestinal Stromal Tumor Regulate KIT Expression and Are Targetable by BET Bromodomain Inhibition," Cancer Res., (2019); 79(5):994-1009.

Hemming, M.L., et al.; "Gastrointestinal stromal tumor enhancers support a transcription factor network predictive of clinical outcome," Proc Natl Acad Sci USA, (2018); 115(25):E5746-E5755.

Hemming, M.L., et al.; "Proteomic Profiling of γ-Secretase Substrates and Mapping of Substrate Requirements," PLoS Biol. (2008); 6(10): e257:2314-2328.

International Preliminary Report on Patentability for International Application No. PCT/US2022/029271 mailed on Nov. 23, 2023, 8 pages.

Kerry J., et al., "MLL-AF4 Spreading Identifies Binding Sites that Are Distinct from Super-Enhancers and that Govern Sensitivity to DOT1L Inhibition in Leukemia," Cell reports , 2017, vol. 18(2), pp. 482-495.

Klossowski, S., et al.; "Menin inhibitor MI-3454 induces remission in MLL1-rearranged and NPM1-mutated models of leukemia," J Clin Invest., (2020); 130(2):981-997.

Krivtsov, A.V., et al.; "A Menin-MLL Inhibitor Induces Specific Chromatin Changes and Eradicates Disease in Models of MLL-Rearranged Leukemia," Cancer Cell (2019); 36(6):660-673.e11, 26 pages.

Le Gall, M., et al.; "Neutralization of KIT Oncogenic Signaling in Leukemia with Antibodies Targeting KIT Membrane Proximal Domain 5," Mol Cancer Ther., (2015); 14(11):2595-2605.

Maki, R.G., et al.; "Key Issues in the Clinical Management of Gastrointestinal Stromal Tumors: an Expert Discussion," Oncologist. (2015); 20(7):823-830.

McGeehan et al., "A first-in-class Menin-MLL1 antagonist for the treatment of MLL-r and NPM1 mutant leukemias," Syndax Pharmaceuticals, Inc., AACR Virtual Annual Meeting, Apr. 27, 2020, retrieved online: https://www.oncozine.com/wp-content/uploads/2020/04/SNDX-5613-AACR-2020-PRESENTATION-vF.pdf, 19 pages.

Medchemexpress, SNDX-5613, 2022, [Retrieved online Sep. 18, 2023] URL: https://web.archive.org/web/20220308174847/https://www.medchemexpress.com/sndx-5613.html; 3 pages.

Paggetti, J., et al.; "Crosstalk between leukemia-associated proteins MOZ and MLL regulates HOX gene expression in human cord blood CD34+ cells," Oncogene. (2010); 29(36):5019-5031.

Shi, X., et al.; "Distinct cellular properties of oncogenic KIT receptor tyrosine kinase mutants enable alternative courses of cancer cell inhibition," Proc Natl Acad Sci USA (2016); 113(33):E4784-4793.

Uckelmann, H.J., et al.; "Therapeutic targeting of preleukemia cells in a mouse model of NPM1 mutant acute myeloid leukemia," Science (2020); 367(6477):586-590, 6 pages.

Xu, S.X., et al.; "Discovery of M-808 as a Highly Potent, Covalent, Small-Molecule Inhibitor of the Menin-MLL Interaction with Strong In Vivo Antitumor Activity," J Med Chem. (2020); 63(9):4997-5010.

(56) References Cited

OTHER PUBLICATIONS

Yang, L., et al.; “Histone H3K4 Methyltransferases as Targets for Drug-Resistant Cancers,” Biology (Basel). (2021); 10(7):581, pp. 1-32.
Borkin et al. “Pharmacologic Inhibition of the Menin-MLL Interaction Blocks Progression of MLL Leukemia In Vivo”, Cancer Cell, vol. 27, p. 589-602 (2015).
Chamberlain et al. “Menin determines K-RAS proliferative outputs in endocrine cells”, The Journal of Clinical Investigation, vol. 124, No. 9, p. 4093-4101 (2014).
Cierpicki T. et al. “Challenges and opportunities in targeting the menin-MLL interaction”, Future Med. Chem. vol. 6, No. 4, p. 447-462 (2014).
Database STN, CAS Registry No. 1048962-49-7 “3-Oxabicyclo[3.1.0]hexan-6-amine, hydrochloride (1:1), (1α,5α,6α)—(CA Index Name)”, Chemical Abstracts Service, American Chemical Society entered Sep. 12, 2008; retrieved Apr. 18, 2023; 1 page.
Database STN, CAS Registry No. 58564-87-7 “7-Oxabicyclo[2.2.1]heptan-2-amine, (1R,2R,4S)-rel—(CA Index Name)”, Chemical Abstracts Service, American Chemical Society entered Nov. 16, 1984; retrieved Apr. 18, 2023; 1 page.
Freedman et al., “Non-Hodgkin’s Lymphomas” Chapter 134, Cancer Medicine, American Cancer Society, B.C. Decker Inc., Hamilton, Ontario, (2003), 30 pages.
Grembecka J. et al. “Menin-MLL inhibitors reverse oncogenic activity of MLL fusion proteins in leukemia”, Nature Chemical Biology, vol. 8, p. 277-284 (2012).
International Preliminary Report on Patentability for International Application No. PCT/US2021/026141 dated Oct. 20, 2022, 7 pages.
International Preliminary Report on Patentability of International Application No. PCT/US2017/036506, issued Dec. 11, 2018, 6 pages.
International Search Report and Written Opinion for International Application No. PCT/US2022/029271, mailed Aug. 2, 2022, 10 pages.
International Search Report and Written Opinion of International Application No. PCT/US2017/036506, mailed on Sep. 11, 2017, 9 pages.
International Search Report and Written Opinion of International Application No. PCT/US2021/026141, mailed Jun. 30, 2021, 8 pages.
Jagtap et al. “Synthesis of (R)-3, 4-dihydro-2H-pyran-2-carboxaldehyde: application to the synthesis of potent adenosine A2A and A3 receptor agonist”, Tetrahedron Letters, (2009); 50(22):2693-2696.
Kang et al. “Enzymatic synthesis of optically active (S)-(+)-2-hydroxymethyl-3, 4-dihydro-2H-pyran and (S)-(+)-2-acetoxymethyl-3, 4-dihydro-2H-pyran”, Tetrahedron: Asymmetry, (1995); 6(1):97-100.
Karageorgis et al. “Activity-Directed Synthesis with Intermolecular Reactions: Development of a Fragment into a Range of Androgen Receptor Agonists”, Angewandte Chemie, International Edition, (2015); 54(46): 13538-13544.
Kress et al. “Chemistry of Pyrimidine. 2. Synthesis of Pyrimidine JV-Oxides and 4-Pyrimidinones by Reaction of 5-Substituted Pyrimidines with Peracids. Evidence for Covalent Hydrates as Reaction Intermediates”, J. Org. Chem., vol. 50, p. 3073-3076 (1985).
Maiti D. et al. “Cu-Catalyzed Arylation of Phenols: Synthesis of Sterically Hindered and Heteroaryl Diaryl Ethers”, J. Org. Chem. vol. 75, p. 1791-1794 (2010).
Malik R. et al. “Targeting the MLL complex in castration-resistant prostate cancer”, Nature Medicine, vol. 21, No. 4, p. 344-354 (2015).
Salvi L. et al. “A New Biarylphosphine Ligand for the Pd-Catalyzed Synthesis of Diaryl Ethers under Mild Conditions”, Organic Letters, vol. 14, No. 1, p. 170-173 (2012).
Shi, A., et al., “Structural Insights into Inhibition of the Bivalent Menin-MLL Interaction by Small Molecules in Leukemia”, Blood, vol. 120(23), pp. 4461-4469.
Yang Y. et al. “Reversal of preexisting hyperglycemia in diabetic mice by acute deletion of the Men1 gene”, PNAS, vol. 107, No. 47, p. 20358-20363 (2010).
Yokoyama A. et al. “The Menin Tumor Suppressor Protein Is an Essential Oncogenic Cofactor for MLL-Associated Leukemogenesis”, Cell, vol. 123, p. 207-218, (2005).
Zhang et al. “Design, synthesis, and preliminary SAR study of 3-and 6-side-chain-extended tetrahydro-pyran analogues of cis-and trans-(6-benzhydryl-tetrahydropyran-3-yl)-benzylamine”, Bioorganic & Medicinal Chemistry, (2006); 14(11):3953-3966.
Arnold et al. “Traditional and emerging antifungal therapies” Proceedings of the American Thoracic Society (2010); 7(3):222-228.
Berge et al. “Pharmaceutical salts” Journal of Pharmaceutical Sciences (1977); 66(1):1-19.
Carter et al. “Menin inhibition decreases Bcl-2 and synergizes with venetoclax in NPM1/FLT3-mutated AML” Blood, The Journal of the American Society of Hematology (2021); 138(17):1637-1641.
Issa et al. “Therapeutic implications of menin inhibition in acute leukemias” Leukemia (2021); 35(9):2482-2495.
JP Office Action for JP Application No. 2022-561040 mailed Apr. 3, 2025, with English Translation, 13 pages.
Kumar et al. “An overview of automated systems relevant in pharmaceutical salt screening” Drug Discovery Today (2007); 12(23-24):1046-1053.
Li et al. “Selective killing of cancer cells by β-lapachone: Direct checkpoint activation as a strategy against cancer” Proceedings of the National Academy of Sciences (2003); 100(5):2674-2678.
Miao et al. “Combinatorial treatment with menin and FLT3 inhibitors induces complete remission in AML models with activating FLT3 mutations” Blood, The Journal of the American Society of Hematology (2020); 136(25):2958-2963.
Miettinen et al. “A nonrandom association between gastrointestinal stromal tumors and myeloid leukemia” Cancer (2007); 112(3):645-649.
Mu et al. “Bromodomain and extraterminal domain inhibitor enhances the antitumor effect of imatinib in gastrointestinal stromal tumours” J. Cell Mol Med. (2020); 24(4):2519-2530, 12 pages.
Patel et al. “NPM1 biology in myeloid neoplasia” Current Hematologic Malignancy Reports (2020); 15(4):350-359.
Revuforj (revumenib), tablets for oral use, 25 mg, 110 mg, 160 mg, Highlights of Prescribing Information / Package Insert / Label, Revised: Nov. 2024 (Nov. 2024), Initial U.S. Approval: 2024, Reference ID: 5479801, Manufactured for: Syndax Pharmaceuticals, Inc., Waltham, MA 02451, USA, 31 pages.
Shi, et al. “Menin-MLL1 Interaction Small Molecule Inhibitors: a Potential Therapeutic Strategy for Leukemia and Cancers” Molecules (2023); 28(7):3026, 15 pages.
Zanger et al., “Cytochrome P450 enzymes in drug metabolism: Regulation of gene expression, enzyme activities, and impact of genetic variation”, *Pharmacology & Therapeutics*, 138 (1), pp. 103-141, Jan. 16, 2013.

* cited by examiner

Patients 04-001 and 05-001 examples
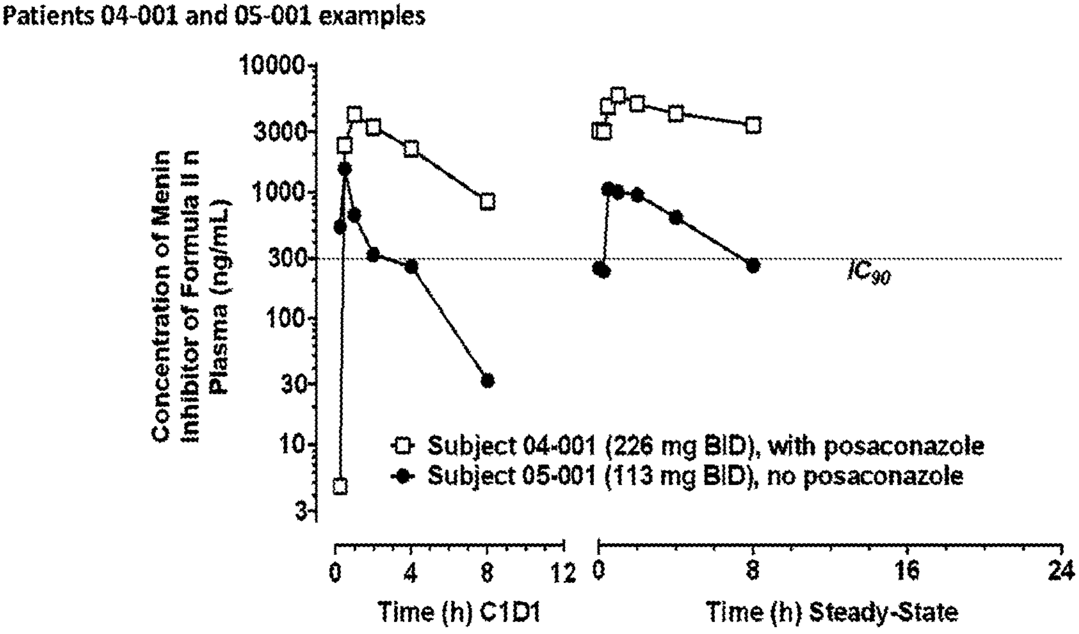
| Subject | Dose | Posaconazole | $ssAUC_{0-24}$ (ng*h/mL) |
|---|---|---|---|
| 05-001 | 113 mg BID | No | 12600 |
| 04-001 | 226 mg BID | Yes | 85700 |

COMBINATIONS OF MENIN INHIBITORS AND CYP3A4 INHIBITORS AND METHODS OF USE THEREOF

CROSS REFERENCE TO RELATED APPLICATIONS

This application is a U.S. National Stage Application under 35 U.S.C. § 371 of International Application No. PCT/US2021/026141, filed on Apr. 7, 2021, which claims priority to, and the benefit of, U.S. Provisional Application No. 63/006,574, filed on Apr. 7, 2020, the contents of which are hereby incorporated by reference in their entireties.

FIELD OF THE INVENTION

The present invention is directed to inhibitors of the interaction of menin with MLL and MLL fusion proteins in combination with one or more CYP3A4 inhibitors, pharmaceutical compositions containing the same, and their use in the treatment of cancer and other diseases mediated by the menin-MLL interaction.

BACKGROUND

The mixed-lineage leukemia (MLL) protein is a histone methyltransferase that is mutated in clinically and biologically distinctive subsets of acute leukemia. Rearranged mixed lineage leukemia (MLL-r) involves recurrent translocations of the 11q23 chromosome locus which lead to an aggressive form of acute leukemia with limited therapeutic options. These translocations target the MLL gene creating an oncogenic fusion protein comprising the amino-terminus of MLL fused in frame with more than 60 different fusion protein partners. Menin, a ubiquitously expressed, nuclear protein encoded by the multiple endocrine neoplasia type 1 (MEN1) tumor suppressor gene, has a high affinity binding interaction with MLL fusion proteins and is an essential co-factor of oncogenic MLL-r fusion proteins (Yokoyama et al., 2005, Cell, 123:207-18; Cierpicki & Grembecka, 2014, Future Med. Chem., 6:447-462). Disruption of this interaction leads to selective growth inhibition and apoptosis of MLL-r leukemia cells both in vitro (Grembecka et al., 2012, Nat. Chem. Biol., 8:277-284) and in vivo (Yokoyama et al., 2005, op. cit.; Borkin et al., 2015, Cancer Cell, 27:589-602).

The menin-MLL complex plays a role in castration-resistant/advanced prostate cancer, and a menin-MLL inhibitor has been shown to reduce tumor growth in vivo (Malik et al., 2015, Nat. Med., 21:344-352). Additionally, a menin-MLL inhibitor has been shown to enhance human β cell proliferation (Chamberlain et al., 2014, J. Clin. Invest., 124:4093-4101), supporting a role for inhibitors of the menin-MLL interaction in the treatment of diabetes (Yang et al., 2010, Proc Natl Acad Sci USA., 107:20358-20363). The interaction between menin and MLL or MLL fusion proteins is an attractive target for therapeutic intervention, and there is a need for novel combination therapeutics that inhibit the menin-HLL interaction for the treatment of various diseases and conditions, including leukemia, other cancers and diabetes.

SUMMARY

The present invention provides a combination therapy comprising a menin inhibitor and a CYP3A inhibitor. In certain embodiments, the invention provides for a pharmaceutical composition comprising: (a) a menin inhibitor, and (b) a CYP3A inhibitor. In some embodiments, the invention is directed to a method for treating a patient comprising (a) administering a menin inhibitor, and (b) administering a CYP3A inhibitor.

Some embodiments of this invention are directed to combination therapies designed to treat or manage cancer in a subject, wherein the combination therapies comprise administering a menin inhibitor in combination with a CYP3A inhibitor. In particular, some embodiments of this invention are directed to methods of treating or managing cancer in a subject, comprising administering a menin inhibitor in combination with a therapeutically effective amount of a CYP3A inhibitor administered simultaneously, separately or sequentially.

In some embodiments, the invention provides a combination therapy comprising a menin inhibitor and a CYP3A4 inhibitor. In certain embodiments, the invention provides for a pharmaceutical composition comprising: (a) a menin inhibitor, and (b) a CYP3A4 inhibitor. In some embodiments, the invention is directed to a method for treating a patient comprising (a) administering a menin inhibitor, and (b) administering a CYP3A4 inhibitor.

Some embodiments of this invention are directed to combination therapies designed to treat or manage cancer in a subject, wherein the combination therapies comprise administering a menin inhibitor in combination with a CYP3A4 inhibitor. In particular, some embodiments of this invention are directed to methods of treating or managing cancer in a subject, comprising administering a menin inhibitor in combination with a therapeutically effective amount of a CYP3A4 inhibitor administered simultaneously, separately or sequentially.

In some embodiments, the CYP3A inhibitor is: an anti-arrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A inhibitor is: posaconazole, alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfinavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; verapamil; telaprevir; vincristine; voriconazole; or any combinations thereof.

In some embodiments, the CYP3A4 inhibitor is posaconazole, cobicistat (GS-9350) or analogs or derivatives of cobicistat (GS-9350). In some embodiments, the CYP3A4 inhibitor is ketoconazole. In some embodiments, the CYP3A4 inhibitor is ritonavir. In some embodiments, the menin inhibitor and the CYP3A4 inhibitor are in separate dosage forms. In some embodiments, the pharmaceutical composition is in a combined dosage form. In some embodiments, the CYP3A4 inhibitor is posaconazole.

In some embodiments, the pharmaceutical composition comprises an amount of the CYP3A4 inhibitor that is effective to increase the oral bioavailability of the menin inhibitor.

In some embodiments, the pharmaceutical composition comprises an amount of the CYP3A4 inhibitor that is effective to increase the $C_{max}$ of the menin inhibitor. In some embodiments, the pharmaceutical composition comprises an amount of the CYP3A4 inhibitor that is effective to increase the $C_{max}$ of the menin inhibitor by about 20× to about 40× the $C_{max}$ of the menin inhibitor administered without a CYP3A4 inhibitor, or about 25× to about 35×. In some embodiments, the pharmaceutical composition comprises an amount of the CYP3A4 inhibitor that is effective to increase the AUC of the menin inhibitor. In some embodiments, the pharmaceutical composition comprises an amount of the CYP3A4 inhibitor that is effective to increase the AUC of the menin inhibitor by about 15× to about 35× the AUC of the menin inhibitor administered without a CYP3A4 inhibitor, or about 20× to about 30×. In some embodiments, the pharmaceutical composition comprises an amount of the CYP3A4 inhibitor that is effective to increase the AUC of the menin inhibitor by about 2× to about 35× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 30× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 25× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 20× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 15× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 10× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 5× the AUC of the menin inhibitor administered without a CYP3A4 inhibitor. In some embodiments, the pharmaceutical composition comprises an amount of the CYP3A4 inhibitor that is effective to increase the AUC of the menin inhibitor by about 2× to about 4× the AUC of the menin inhibitor administered without a CYP3A4 inhibitor.

In some embodiments, the pharmaceutical composition further comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the pharmaceutical composition further comprises cyclophosphamide, hydroxydaunorubicin, vincristine, and prednisone, and optionally, rituximab. In some embodiments, the pharmaceutical composition further comprises bendamustine, and rituximab. In some embodiments, the pharmaceutical composition further comprises fludarabine, cyclophosphamide, and rituximab. In some embodiments, the pharmaceutical composition further comprises cyclophosphamide, vincristine, and prednisone, and optionally, rituximab. In some embodiments, the pharmaceutical composition further comprises etoposide, doxorubicin, vincristine, cyclophosphamide, prednisolone, and optionally, rituximab. In some embodiments, the pharmaceutical composition further comprises dexamethasone and lenalidomide.

Disclosed herein, in certain embodiments, is a pharmaceutical combination comprising a therapeutically-effective amount of the menin inhibitor and a CYP3A4 inhibitor. In some embodiments, the combination is in a combined dosage form. In some embodiments, the combination is in separate dosage forms. In some embodiments, the menin inhibitor and the CYP3A4 inhibitor are administered concurrently. In some embodiments, the menin inhibitor and the CYP3A4 inhibitor are administered simultaneously, essentially simultaneously or within the same treatment protocol. In some embodiments, the menin inhibitor and the CYP3A4 inhibitor are administered sequentially. In some embodiments, the CYP3A4 inhibitor is: an anti-arrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A4 inhibitor is: alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfmavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; verapamil; troleandromycin; vincristine; voriconazole; or any combinations thereof.

In some embodiments, the CYP3A4 inhibitor is cobicistat (GS-9350) or analogs or derivatives of cobicistat (GS-9350). In some embodiments, the CYP3A4 inhibitor is ketoconazole. In some embodiments, the CYP3A4 inhibitor is ritonavir.

In some embodiments, the pharmaceutical combination comprises an amount of the CYP3A4 inhibitor that is effective to increase the oral bioavailability of the menin inhibitor. In some embodiments, the pharmaceutical combination comprises an amount of the CYP3A4 inhibitor that is effective to increase the $C_{max}$ of the menin inhibitor. In some embodiments, the pharmaceutical combination comprises an amount of the CYP3A4 inhibitor that is effective to increase the $C_{max}$ of the menin inhibitor by about 20× to about 40× the $C_{max}$ of the menin inhibitor administered without a CYP3A4 inhibitor, or about 25× to about 35×. In some embodiments, the pharmaceutical combination comprises an amount of the CYP3A4 inhibitor that is effective to increase the AUC of the menin inhibitor. In some embodiments, the pharmaceutical combination comprises an amount of the CYP3A4 inhibitor that is effective to increase the AUC of the menin inhibitor by about 15× to about 35× the AUC of the menin inhibitor administered without a CYP3A4 inhibitor, or about 20× to about 30×. In some embodiments, the pharmaceutical combination comprises an amount of the CYP3A4 inhibitor that is effective to increase the AUC of the menin inhibitor by about 2× to about 30× the AUC of the menin inhibitor administered without a CYP3A4 inhibitor. In some embodiments, the pharmaceutical combination comprises an amount of the CYP3A4 inhibitor that is effective to increase the AUC of the menin inhibitor by about 2× to about 25× the AUC of the menin inhibitor administered without a C YP3A4 inhibitor. In some embodiments, the pharmaceutical combination comprises an amount of the CYP3A4 inhibitor that is effective to increase the AUC of the menin inhibitor by about 2× to about 20× the AUC of the menin inhibitor administered without a CYP3A4 inhibitor. In some embodiments, the pharmaceutical combination comprises an amount of the CYP3A4 inhibitor that is effective to increase the AUC of the menin inhibitor by about 2× to about 15× the AUC of the menin inhibitor administered without a CYP3A4 inhibitor. In some embodiments, the pharmaceutical combination comprises an amount of the CYP3A4 inhibitor that is effective to increase the AUC of the menin inhibitor by about 2× to about 10× the AUC of the menin inhibitor administered without a CYP3A4 inhibitor. In some embodiments, the pharmaceutical combination comprises an amount of the CYP3A4 inhibitor that is effective to increase the AUC of the menin inhibitor by about 2× to about 5× the AUC of the menin inhibitor administered without a CYP3A4 inhibitor. In some embodiments, the pharmaceutical combination comprises an amount of the CYP3A4 inhibitor that is effective to increase the AUC of the menin inhibitor by about 2× to about 4× the AUC of the menin inhibitor administered without a CYP3A4 inhibitor.

In some embodiments, the pharmaceutical combination further comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the pharmaceutical combination further comprises cyclophosphamide, hydroxydaunorubicin, vincristine, and prednisone, and optionally, rituximab. In some embodiments, the pharmaceutical combination further comprises bendamustine, and rituximab. In some embodiments, the pharmaceutical combination further comprises fludarabine, cyclophosphamide, and rituximab. In some embodiments, the pharmaceutical combination further comprises cyclophosphamide, vincristine, and prednisone, and optionally, rituximab. In some embodiments, the pharmaceutical combination further comprises etoposide, doxorubicin, vincristine, cyclophosphamide, prednisolone, and optionally, rituximab. In some embodiments, the pharmaceutical combination further comprises dexamethasone and lenalidomide.

In some embodiments, the CYP3A4 inhibitor is: an antiarrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A4 inhibitor is: alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfmavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; troleandromycin; verapamil; telaprevir; vincristine; voriconazole; or any combinations thereof.

In some embodiments, the CYP3A4 inhibitor is posaconazole. In some embodiments, the CYP3A4 inhibitor is cobicistat (GS-9350) or analogs or derivatives of cobicistat (GS-9350). In some embodiments, the CYP3A4 inhibitor is ketoconazole. In some embodiments, the CYP3A4 inhibitor is ritonavir.

In some embodiments, the daily dosage of the menin inhibitor is between about 10 mg to about 500 mg. In some embodiments, the daily dosage of the menin inhibitor is between about 200 mg and about 500 mg. In some embodiments, the daily dosage of the menin inhibitor is between about 250 mg and about 460 mg. In some embodiments, the daily dosage amount of the menin inhibitor is about 226 mg. In some embodiments, the daily dosage of the menin inhibitor is 452 mg.

In some embodiments, the method comprises an amount of the CYP3A4 inhibitor that is effective to increase the oral bioavailability of the menin inhibitor. In some embodiments, the method comprises an amount of the CYP3A4 inhibitor that is effective to increase the $C_{max}$ of the menin inhibitor. In some embodiments, the method comprises an amount of the CYP3A4 inhibitor that is effective to increase the $C_{max}$ of the menin inhibitor by about 20× to about 40× the $C_{max}$ of the menin inhibitor administered without a CYP3A4 inhibitor, or about 25× to about 35×. In some embodiments, the method comprises an amount of the CYP3A4 inhibitor that is effective to increase the AUC of the menin inhibitor. In some embodiments, the method comprises an amount of the CYP3A4 inhibitor that is effective to increase the AUC of the menin inhibitor by about 15× to about 35× the AUC of the menin inhibitor administered without a CYP3A4 inhibitor, or about 20× to about 30×. In some embodiments, the method comprises an amount of the CYP3A4 inhibitor that is effective to increase the AUC of the menin inhibitor by about 2× to about 35× the AUC of the menin inhibitor administered without a CYP3A4 inhibitor. In some embodiments, the method comprises an amount of the CYP3A4 inhibitor that is effective to increase the AUC of the menin inhibitor by about 2× to about 30× the AUC of the menin inhibitor administered without a CYP3A4 inhibitor. In some embodiments, the method comprises an amount of the CYP3A4 inhibitor that is effective to increase the AUC of the menin inhibitor by about 2× to about 25× the AUC of the menin inhibitor administered without a CYP3A4 inhibitor. In some embodiments, the method comprises an amount of the CYP3A4 inhibitor that is effective to increase the AUC of the menin inhibitor by about 2× to about 20× the AUC of the menin inhibitor administered without a CYP3A4 inhibitor. In some embodiments, the method comprises an amount of the CYP3A4 inhibitor that is effective to increase the AUC of the menin inhibitor by about 2× to about 15× the AUC of the menin inhibitor administered without a CYP3A4 inhibitor. In some embodiments, the method comprises an amount of the CYP3A4 inhibitor that is effective to increase the AUC of the menin inhibitor by about 2× to about 10× the AUC of the menin inhibitor administered without a CYP3A4 inhibitor. In some embodiments, the method comprises an amount of the CYP3A4 inhibitor that is effective to increase the AUC of the menin inhibitor by about 2× to about 5× the AUC of the menin inhibitor administered without a CYP3A4 inhibitor. In some embodiments, the method comprises an amount of the CYP3A4 inhibitor that is effective to increase the AUC of the menin inhibitor by about 2× to about 4× the AUC of the menin inhibitor administered without a CYP3A4 inhibitor. In some embodiments, the method comprises the pharmaceutical combination does not significantly affect the $T_{max}$ or T ½ of the menin inhibitor as compared to the $T_{max}$ and $T_{1/2}$ of the menin inhibitor administered without a CYP3A4 inhibitor. In some embodiments, the menin inhibitor and the CYP3A4 inhibitor are in a combined dosage form. In some embodiments, the menin inhibitor and the CYP3A4 inhibitor are in separate dosage forms. In some embodiments, the menin inhibitor and the CYP3A4 inhibitor are administered concurrently. In some embodiments, the menin inhibitor and the CYP3A4 inhibitor are administered simultaneously, essentially simultaneously or within the same treatment protocol. In some embodiments, the menin inhibitor and the CYP3A4 inhibitor are administered sequentially.

BRIEF DESCRIPTION OF THE FIGURES

FIG. 1 illustrates the change in steady state AUC following oral administration of the menin inhibitor of Formula II with and without CYP3A4 inhibitor, posaconazole.

DETAILED DESCRIPTION OF THE INVENTION

Small molecule menin inhibitors administered in combination with CYP3A4 inhibitors act together to treat a variety of diseases affected by or affecting many cell types.

In some embodiments, the invention provides a combination therapy comprising a menin inhibitor and a CYP3A4 inhibitor. In some embodiments, the invention provides for a pharmaceutical composition comprising: (a) a menin inhibitor, and (b) a CYP3A4 inhibitor. In some embodiments, the invention is directed to a method for treating a patient comprising (a) administering a menin inhibitor, and (b) administering a CYP3A4 inhibitor. In some embodiments, the invention is directed to a method for treating a patient comprising (a) administering a pharmaceutical composition comprising a menin inhibitor, and (b) administering a pharmaceutical composition comprising a CYP3A4 inhibitor.

Some embodiments of this invention is directed to combination therapies designed to treat or manage cancer in a subject, wherein the combination therapies comprise administering a menin inhibitor in combination with a CYP3A4 inhibitor. In particular, some embodiments of this invention is directed to methods of treating or managing cancer in a subject, comprising administering a menin inhibitor in combination with a therapeutically effective amount of a CYP3A4 inhibitor administered simultaneously, separately or sequentially.

In some embodiments, the combination therapy increases plasma levels of the menin inhibitor. In some embodiments, the combination therapy enhances inhibitor efficacy to treat a variety of diseases. In some embodiments, the combination therapy acts synergistically to treat cancer. In some embodiments, combination therapy enhances, increases or prolongs either potency or duration of therapeutic effect. In some embodiments, the CYP3A4 inhibitor enhances, increases, and/or prolongs the efficacy or duration of the menin inhibitor's therapeutic effect.

In some embodiments, the menin inhibitor is 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (Formula I), or a pharmaceutically acceptable salt, stereoisomer, geometric isomer or tautomer thereof. In some embodiments, the menin inhibitor is N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide (Formula II), or a pharmaceutically acceptable salt, stereoisomer, geometric isomer or tautomer thereof. In some embodiments, the menin inhibitor embodies any stereoisomers, geometric isomers and/or tautomers. According to the invention as disclosed herein, the menin inhibitors are selected from Formula (I) and Formula (II)

Formula (I)

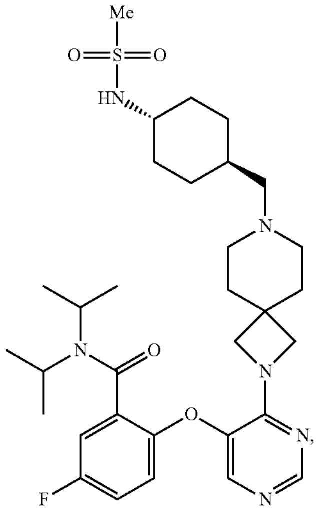

Formula (II)

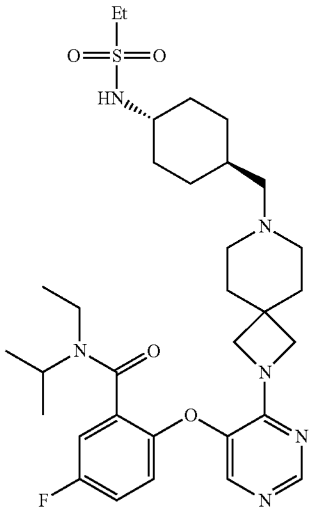

or a pharmaceutically acceptable salt, stereoisomer, geometric isomer or tautomer thereof.

Formula (I) is also described by the chemical name 5-fluoro-N,N-diisopropyl-2-((4-(7-((trans-4-(methylsulfonamido)cyclohexyl)methyl)-2,7-diazaspiro[3.5]nonan-2-yl)pyrimidin-5-yl)oxy)benzamide. Formula (II) is also described by the chemical name N-ethyl-2-((4-(7-((trans-4-(ethylsulfonamido)cyclohexyl)methyl)-2,7-diazaspiro[3.5]nonan-2-yl)pyrimidin-5-yl)oxy)-5-fluoro-N-isopropylbenzamide.

In some embodiments, the pharmaceutically acceptable salt is a bis-methanesulfonic acid salt. In some embodiments, the pharmaceutically acceptable salt is a bis-hydrochloric acid salt. In some embodiments, the pharmaceutically acceptable salt is a sesquifumaric acid salt.

In some embodiments, the menin inhibitor is therapeutically effective at a lower dose when combined with the CYP3A4 inhibitor. In some embodiments, the menin inhibitor is more effective in combination with a CYP3A4 inhibitor.

In some embodiments, the menin inhibitor is administered in combination with a CYP3A4 inducer. In some embodiments, CYP3A4 inducers include but are not limited to one or more of avasimibe, phenytoin, carbamazepine, rifampin, enzalutamide, and St John's wort.

In some embodiments, the menin inhibitor is Formula I and the CYP3A4 inhibitor is an azole antifungal. In some embodiments, the menin inhibitor is Formula II and the CYP3A4 inhibitor is an azole antifungal.

In some embodiments, the menin inhibitor is Formula I and the CYP3A4 inhibitor is posaconazole. In some embodiments, the menin inhibitor is Formula II and the CYP3A4 inhibitor is posaconazole.

Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. In this application, the use of "or" means "and/or" unless stated otherwise.

Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

"Bioavailability" refers to the percentage of the menin inhibitor dosed that is delivered into the general circulation of the animal or human being studied. The total exposure (AUC(0-∞)) of a drug when administered intravenously is usually defined as 100% bioavailable (F %). "Oral bioavailability" refers to the extent to which the menin inhibitor is absorbed into the general circulation when the pharmaceutical composition is taken orally as compared to intravenous injection.

"Blood plasma concentration" refers to the concentration of the menin inhibitor in the plasma component of blood of a subject. It is understood that the plasma concentration of the menin inhibitor may vary significantly between subjects, due to variability with respect to metabolism and/or possible interactions with other therapeutic agents. In accordance with some embodiments disclosed herein, the blood or plasma concentration of the menin inhibitor may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of the menin inhibitor may vary from subject to subject.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the menin inhibitor, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician. The terms "subject", "patient" and "individual" are used interchangeably. As used herein, they refer to an animal. By way of example only, a subject may be, but is not limited to, a mammal including, but not limited to, a human. The terms do not require the supervision (whether continuous or intermittent) of a medical professional.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the IC50 refers to an amount, concentration or dosage of a particular test compound that achieves a 50% inhibition of a maximal response, such as inhibition of menin, in an assay that measures such response.

As used herein, EC50 refers to a dosage, concentration or amount of a particular test compound that elicits a dose-dependent response at 50% of maximum expression of a particular response that is induced, provoked or potentiated by the particular test compound.

A wide variety of pharmaceutically acceptable salts is formed from the menin inhibitor and includes: acid addition salts formed by reacting the menin inhibitor with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like; acid addition salts formed by reacting the menin inhibitor with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to the menin inhibitor refers to a salt of the menin inhibitor, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In some embodiments, solvates of the menin inhibitor, or pharmaceutically acceptable salts thereof, are conveniently prepared or formed during the processes described herein. In some embodiments, solvates of the menin inhibitor are anhydrous. In some embodiments, the menin inhibitor, or pharmaceutically acceptable salts thereof, exist in unsolvated form. In some embodiments, the menin inhibitor, or pharmaceutically acceptable salts thereof, exist in unsolvated form and are anhydrous.

In yet other embodiments, the menin inhibitor, or a pharmaceutically acceptable salt thereof, is prepared in various forms, including but not limited to, amorphous phase, crystalline forms, milled forms and nano-particulate forms. In some embodiments, the menin inhibitor, or a pharmaceutically acceptable salt thereof, is amorphous. In some embodiments, the menin inhibitor, or a pharmaceutically acceptable salt thereof, is amorphous and anhydrous. In some embodiments, the menin inhibitor, or a pharmaceutically acceptable salt thereof, is crystalline. In some embodiments, the menin inhibitor, or a pharmaceutically acceptable salt thereof, is crystalline and anhydrous.

General CYP3A Inhibitors

Disclosed herein, in certain embodiments, are pharmaceutical combinations comprising a menin inhibitor and a CYP3A inhibitor. Further disclosed herein, in certain embodiments, are combinations comprising a pharmaceutical composition of the menin inhibitor and a pharmaceutical composition CYP3A inhibitor.

Cytochrome P450 3A (abbreviated CYP3A), is a member of the cytochrome P450 mixed-function oxidase system. The CYP3A locus includes all the known members of the 3A subfamily of the cytochrome P450 superfamily of genes. These genes encode monooxygenases which catalyze many reactions involved in drug metabolism and synthesis of cholesterol, steroids and other lipids. The CYP3A cluster consists of four genes; CYP3A4, CYP3A5, CYP3A7, and CYP3A43.

Cytochrome P450 enzymes modify a variety of substrate, including hydroxylation, epoxidation, aromatic oxidations, heteroatom oxidations, N- and O-dealkylations, aldehyde oxidations, and dehydrogenations.

In some embodiments, the menin inhibitor and CYP3A inhibitor are co-administered concurrently (e.g., simultaneously, essentially simultaneously or within the same treatment protocol) or sequentially.

In some embodiments, the menin inhibitor and CYP3A inhibitor are co-administered in separate dosage forms. In some embodiments, the menin inhibitor and a CYP3A inhibitor are co-administered in combined dosage forms.

In some embodiments, the co-administration of the menin inhibitor and a CYP3A inhibitor increases the oral bioavailability of the menin inhibitor. In some embodiments, the co-administration of the menin inhibitor and a CYP3A inhibitor increases the $C_{max}$ of the menin inhibitor. In some embodiments, the coadministration of the menin inhibitor and a CYP3A inhibitor increases the AUC of the menin inhibitor. In some embodiments, the coadministration of the menin inhibitor and a CYP3A inhibitor increases the $T_{1/2}$ of the menin inhibitor.

Compositions or therapies disclosed herein may be administered individually to a patient or may be administered in combination (e.g. simultaneously, sequentially or separately). In some embodiments, the CYP3A4 inhibitor is administered in advance of the menin inhibitor. In some embodiments, the CYP3A4 inhibitor is administered before the menin inhibitor. In some embodiments, the CYP3A4 inhibitor is posaconazole and is administered in advance of the menin inhibitor of Formula II.

In some embodiments, the menin inhibitor and the CYP3A inhibitor are administered in temporal proximity (e.g., the menin inhibitor and the CYP3A inhibitor can be initially administered simultaneously). Accordingly, the present disclosure provides a method of treating or preventing cancer comprising administering the menin inhibitor and the CYP3A inhibitor in temporal proximity. In some embodiments, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent.

In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

"Combination therapy" is intended to embrace administration of the therapeutic agents disclosed herein in a sequential or simultaneous manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed or variable ratio of each therapeutic agent or in multiple, single capsules for each of the therapeutic agents. Sequential or substantially simultaneous administration of each therapeutic agent can be affected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered can vary. Therapeutic agents may also be administered in alternation.

In some embodiments, the disclosure provides a synergistic combination of the menin inhibitor and the CYP3A inhibitor, wherein the menin inhibitor and the CYP3A inhibitor come into contact with each other in the human body (e.g., only in the human body). In some embodiments, the disclosure provides a method of preparing a combination therapy by bringing the menin inhibitor and the CYP3A inhibitor into contact with each other at a locus. In some embodiments, the method of preparing a combination therapy by bringing the menin inhibitor and the CYP3A inhibitor into contact with each other at a locus occurs in the human body (e.g., only in the human body).

Disclosed herein, in some embodiments, the CYP3A inhibitor is a CYP3A4 inhibitor. In some embodiments, the CYP3A inhibitor is a CYP3A5 inhibitor. In some embodiments, the CYP3A inhibitor is a CYP3A7 inhibitor.

Combination with CYP3A4 Inhibitors

Disclosed herein, in certain embodiments, are combinations comprising a menin inhibitor and a CYP3A4 inhibitor.

Further disclosed herein, in certain embodiments, are pharmaceutical combinations comprising a menin inhibitor and a CYP3A4 inhibitor.

Cytochrome P450 3A4 (abbreviated CYP3A4) (EC 1.14.13.97), is a member of the cytochrome P450 mixed-function oxidase system. Cytochrome P450 proteins are monooxygenases that catalyze many reactions involved in drug metabolism. CYP3A4 is encoded by the CYP3A4 gene. This gene is part of a cluster of cytochrome P450 genes on chromosome 7q21.1. CYP3A4 is involved in the oxidation of a large range of substrates, for example the menin inhibitor.

Cytochrome P450 enzymes modify a variety of substrate, including hydroxylation, epoxidation, aromatic oxidations, heteroatom oxidations, N- and O-dealkylations, aldehyde oxidations, and dehydrogenations.

In some embodiments, the menin inhibitor and a CYP3A4 inhibitor are co-administration concurrently (e.g., simultaneously, essentially simultaneously or within the same treatment protocol) or sequentially.

In some embodiments, the menin inhibitor and a CYP3A4 inhibitor are co-administered in separate dosage forms. In some embodiments, the menin inhibitor and a CYP3A4 inhibitor are coadministered in combined dosage forms.

In some embodiments, the co-administration of the menin inhibitor and a CYP3A4 inhibitor increases the oral bioavailability of the menin inhibitor. In some embodiments, the co-administration of the menin inhibitor and a CYP3A4 inhibitor increases the $C_{max}$ of the menin inhibitor. In some embodiments, the co-administration of the menin inhibitor and a CYP3A4 inhibitor increases the AUC of the menin inhibitor.

In some embodiments, co-administration of the menin inhibitor and a CYP3A4 inhibitor increases the $C_{max}$ of the menin inhibitor by about 20× to about 40× the $C_{max}$ of the menin inhibitor administered without a CYP3A4 inhibitor. In some embodiments, co-administration of the menin inhibitor and a CYP3A4 inhibitor increases the $C_{max}$ of the menin inhibitor by about 25× to about 35×. In some embodiments, coadministration of the menin inhibitor and a CYP3A4 inhibitor increases the $C_{max}$ of the menin inhibitor by about 20×. In some embodiments, co-administration of the menin inhibitor and a CYP3A4 inhibitor increases the $C_{max}$ of the menin inhibitor by about 21×. In some embodiments, co-administration of the menin inhibitor and a CYP3A4 inhibitor increases the $C_{max}$ of the menin inhibitor by about 22×. In some embodiments, coadministration of the menin inhibitor and a CYP3A4 inhibitor increases the $C_{max}$ of the menin inhibitor by about 23×. In some embodiments, co-administration of the menin inhibitor and a CYP3A4 inhibitor increases the $C_{max}$ of the menin inhibitor by about 24×. In some embodiments, co-administration of the menin inhibitor and a CYP3A4 inhibitor increases the $C_{max}$ of the menin inhibitor by about 25×. In some embodiments, coadministration of the menin inhibitor and a CYP3A4 inhibitor increases the $C_{max}$ of the menin inhibitor by about 26×. In some embodiments, co-administration of the menin inhibitor and a CYP3A4 inhibitor increases the $C_{max}$ of the menin inhibitor by about 27×. In some embodiments, co-administration of the menin inhibitor and a CYP3A4 inhibitor increases the $C_{max}$ of the menin inhibitor by about 28×. In some embodiments, coadministration of the menin inhibitor and a CYP3A4 inhibitor increases the $C_{max}$ of the menin inhibitor by about 29×. In some embodiments, co-administration of the menin inhibitor and a CYP3A4 inhibitor increases the $C_{max}$ of the menin inhibitor by about 30×. In some embodiments, co-administration of the menin inhibitor and a CYP3A4 inhibitor increases the $C_{max}$ of the menin inhibitor by about 30×. In some embodiments, coadministration of the menin inhibitor and a CYP3A4 inhibitor increases the $C_{max}$ of the menin inhibitor by about 32×. In some embodiments, co-administration of the menin inhibitor and a CYP3A4 inhibitor increases the $C_{max}$ of the menin inhibitor by about 33×. In some embodiments, co-administration of the menin inhibitor and a CYP3A4 inhibitor increases the $C_{max}$ of the menin inhibitor by about 34×. In some embodiments, coadministration of the menin inhibitor and a CYP3A4 inhibitor increases the $C_{max}$ of the menin inhibitor by about 35×. In some embodiments, co-administration of the menin inhibitor and a CYP3A4 inhibitor increases the $C_{max}$ of the menin inhibitor by about 36×. In some embodiments, co-administration of the menin inhibitor and a CYP3A4 inhibitor increases the $C_{max}$ of the menin inhibitor by about 37×. In some embodiments, coadministration of the menin inhibitor and a CYP3A4 inhibitor increases the $C_{max}$ of the menin inhibitor by about 38×. In some embodiments, co-administration of the menin inhibitor and a CYP3A4 inhibitor increases the $C_{max}$ of the menin inhibitor by about 39×. In some embodiments, co-administration of the menin inhibitor and a CYP3A4 inhibitor increases the $C_{max}$ of the menin inhibitor by about 40×.

In some embodiments, the co-administration of the menin inhibitor and a CYP3A4 inhibitor increases the AUC of the menin inhibitor by about 15× to about 35× the AUC of the menin inhibitor administered without a CYP3A4 inhibitor. In some embodiments, co-administration of the menin inhibitor and a CYP3A4 inhibitor increases the AUC of the menin inhibitor by about 20× to about 30×. In some embodiments, co-administration of the menin inhibitor and a CYP3A4 inhibitor increases the AUC of the menin inhibitor by about 2× to about 35× the AUC of the menin inhibitor administered without a CYP3A4 inhibitor. In some embodiments, co-administration of the menin inhibitor and a CYP3A4 inhibitor increases the AUC of the menin inhibitor by about 2× to about 30× the AUC of the menin inhibitor administered without a CYP3A4 inhibitor. In some embodiments, co-administration of the menin inhibitor and a CYP3A4 inhibitor increases the AUC of the menin inhibitor by about 2× to about 25× the AUC of the menin inhibitor administered without a CYP3A4 inhibitor. In some embodiments, co-administration of the menin inhibitor and a CYP3A4 inhibitor increases the AUC of the menin inhibitor by about 2× to about 20× the AUC of the menin inhibitor administered without a CYP3A4 inhibitor. In some embodiments, coadministration of the menin inhibitor and a CYP3A4 inhibitor increases the AUC of the menin inhibitor by about 2× to about 15× the AUC of the menin inhibitor administered without a CYP3A4 inhibitor. In some embodiments, co-administration of the menin inhibitor and a CYP3A4 inhibitor increases the AUC of the menin inhibitor by about 2× to about 10× the AUC of the menin inhibitor administered without a CYP3A4 inhibitor. In some embodiments, co-administration of the menin inhibitor and a CYP3A4 inhibitor increases the AUC of the menin inhibitor by about 2× to about 5× the AUC of the menin inhibitor administered without a CYP3A4 inhibitor. In some embodiments, co-administration of the menin inhibitor and a CYP3A4 inhibitor increases the AUC of the menin inhibitor by about 2× to about 4× the AUC of the menin inhibitor administered without a CYP3A4 inhibitor. In some embodiments, co-administration of the menin inhibitor and a CYP3A4 inhibitor increases the AUC of the menin inhibitor by about 15×. In some embodiments, co-administration of the menin inhibitor and a CYP3A4 inhibitor increases the AUC of the menin inhibitor by about 2×. In some embodiments, co-administration of the menin inhibitor and a CYP3A4 inhibitor increases the AUC of the menin inhibitor by about 3×. In some embodiments, co-administration of the menin inhibitor and a CYP3A4 inhibitor increases the AUC of the menin inhibitor by about 4×. In some embodiments, coadministration of the menin inhibitor and a CYP3A4 inhibitor increases the AUC of the menin inhibitor by about 5×. In some embodiments, co-administration of the menin inhibitor and a CYP3A4 inhibitor increases the AUC of the menin inhibitor by about 6×. In some embodiments, coadministration of the menin inhibitor and a CYP3A4 inhibitor increases the AUC of the menin inhibitor by about 7×. In some embodiments, coadministration of the menin inhibitor and a CYP3A4 inhibitor increases the AUC of the menin inhibitor by about 8×. In some embodiments, co-administration of the menin inhibitor and a CYP3A4 inhibitor increases the AUC of the menin inhibitor by about 9×. In some embodiments, co-administration of the menin inhibitor and a CYP3A4 inhibitor increases the AUC of the menin inhibitor by about 10×. In some embodiments, coadministration of the menin inhibitor and a CYP3A4 inhibitor increases the AUC of the menin inhibitor by about 11×. In some embodiments, co-administration of the menin inhibitor and a CYP3A4 inhibitor increases the AUC of the menin inhibitor by about 12×. In some embodiments, co-administration of the menin inhibitor and a CYP3A4 inhibitor increases the AUC of the menin inhibitor by about 13×. In some embodiments, coadministration of the menin inhibitor and a CYP3A4 inhibitor increases the AUC of the menin inhibitor by about 14×. In some embodiments, co-administration of the menin inhibitor and a CYP3A4 inhibitor increases the AUC of the menin inhibitor by about 15×. In some embodiments, co-administration of the menin inhibitor and a CYP3A4 inhibitor increases the AUC of the menin inhibitor by about 16×. In some embodiments, coadministration of the menin inhibitor and a CYP3A4 inhibitor increases the AUC of the menin inhibitor by about 17×. In some embodiments, co-administration of the menin inhibitor and a CYP3A4 inhibitor increases the AUC of the menin inhibitor by about 18×. In some embodiments, co-administration of the menin inhibitor and a CYP3A4 inhibitor increases the AUC of the menin inhibitor by about 19×. In some embodiments, coadministration of the menin inhibitor and a CYP3A4 inhibitor increases the AUC of the menin inhibitor by about 20×. In some embodiments, co-administration of the menin inhibitor and a CYP3A4 inhibitor increases the AUC of the menin inhibitor by about 2 IX. In some embodiments, co-administration of the menin inhibitor and a CYP3A4 inhibitor increases the AUC of the menin inhibitor by about 22×. In some embodiments, coadministration of the menin inhibitor and a CYP3A4 inhibitor increases the AUC of the menin inhibitor by about 23×. In some embodiments, co-administration of the menin inhibitor and a CYP3A4 inhibitor increases the AUC of the menin inhibitor by about 24×. In some embodiments, co-administration of the menin inhibitor and a CYP3A4 inhibitor increases the AUC of the menin inhibitor by about 25×. In some embodiments, coadministration of the menin inhibitor and a CYP3A4 inhibitor increases the AUC of the menin inhibitor by about 26×. In some embodiments, co-administration of the menin inhibitor and a CYP3A4 inhibitor increases the AUC of the menin inhibitor by about 27×. In some embodiments, co-administration of the menin inhibitor and a CYP3A4 inhibitor increases the AUC of the menin inhibitor by about 28×. In some embodiments, coadministration of the menin inhibitor and a CYP3A4 inhibitor increases the AUC of the menin inhibitor by about 29×. In some embodiments, co-administration of the menin inhibitor and a CYP3A4 inhibitor increases the AUC of the menin inhibitor by about 30×. In some embodiments, co-administration of the menin inhibitor and a CYP3A4 inhibitor increases the AUC of the menin inhibitor by about 3 IX. In some embodiments, coadministration of the menin inhibitor and a CYP3A4 inhibitor increases the AUC of the menin inhibitor by about 32×. In some embodiments, co-administration of the menin inhibitor and a CYP3A4 inhibitor increases the AUC of the menin inhibitor by about 33×. In some embodiments, co-administration of the menin inhibitor and a CYP3A4 inhibitor increases the AUC of the menin inhibitor by about 34×. In some embodiments, coadministration of the menin inhibitor and a CYP3A4 inhibitor increases the AUC of the menin inhibitor by about 35×.

Any suitable daily dose of a CYP3A4 inhibitor is contemplated for use with the compositions, dosage forms, and methods disclosed herein. For example, the daily dose of the CYP3A4 inhibitor depends of the strength of the CYP3A4 inhibitor. Weak CYP3A4 inhibitors (e.g. cimetidine) will require higher daily doses than moderate CYP3A4 inhibitors (e.g., erythromycin, grapefruit juice, verapamil, diltiazem), and moderate CYP3A4 inhibitors will require higher daily doses than strong CYP3A4 inhibitors (e.g., indinavir, nelfmavir, ritonavir, clarithromycin, itraconazole, ketoconazole, nefazodone).

Exemplary CYP3A4 Inhibitors

In some embodiments, the menin inhibitor is co-administered with CYP3A4 inhibitor selected from an anti-arrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof.

In some embodiments, at least one CYP3A4 inhibitor is selected from the compounds disclosed in one or more of the following patent applications assigned to *Sequoia* Pharmaceuticals, Inc., the disclosure of each of which is incorporated herein by reference: U.S. Patent Publication No. US 2005/0209301 and U.S. Patent Publication No. US 2005/0267074. In some embodiments, at least one CYP3A4 inhibitor is selected from the compounds disclosed in one or more of the following patents and patent applications assigned to Bioavailability Systems, LLC, the disclosure of each of which is incorporated herein by reference: US 2004058982, U.S. Pat. Nos. 6,248,776, 6,063,809, 6,054,477, 6,162,479, WO 2000054768, U.S. Pat. Nos. 6,309,687, 6,476,066, 6,660,766, WO 2004037827, U.S. Pat. Nos. 6,124,477, 5,820,915, 5,993,887, 5,990,154, 6,255,337.

In some embodiments, the menin inhibitor is co-administered with posaconazole, conivaptan, lopinavir, alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delavirdine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfmavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; verapamil; telaprevir; troleandromycin, vincristine; voriconazole; or any combinations thereof. In some embodiments, the menin inhibitor is co-administered with cobicistat (GS-9350) or analogs or derivatives of cobicistat (GS-9350). In some embodiments, the menin inhibitor is co-administered with ketoconazole. In some embodiments, the menin inhibitor is co-administered with ritonavir. Diazepam→3-OH refers to 3-hydroxydiazepam and quinidine→3-OH refers to 3-hydroxyquinidine. In some embodiments, the CYP3A4 inhibitor is a pharmaceutically acceptable salt of one or more of the listed above or below.

Any suitable CYP3A4 inhibitor is contemplated for use with the compositions, dosage forms, and methods disclosed herein. The selection of the CYP3A4 inhibitor depends on multiple factor. For example, factors to be considered include the desired reduction in the daily dose of the menin inhibitor, any additional drug interactions of the CYP3A4 inhibitor, and the length for which the CYP3A4 inhibitor may be taken. In certain instances, the CYP3A4 inhibitor is a CYP3A4 inhibitor which may be taken long-term, for example chronically. In some embodiments, the CYP3A4 inhibitor is taken for a limited time and the menin inhibitor is taken chronically.

Disclosed herein, in certain embodiments, are methods of increasing the $C_{max}$ of the menin inhibitor comprising co-administering a combination of the menin inhibitor and a CYP3A4 inhibitor. In some embodiments, $C_{max}$ of the menin inhibitor is increased by about 20× to about 40× the $C_{max}$ of the menin inhibitor administered without a CYP3A4 inhibitor, or about 25× to about 35×. In some embodiments, the method increases the AUC of the menin inhibitor. In some embodiments, the method increases the AUC of the menin inhibitor by about 15× to about 35× the AUC of the menin inhibitor administered without a CYP3A4 inhibitor, or about 20× to about 30×. In some embodiments, the method increases the AUC of the menin inhibitor by about 2× to about 35× the AUC of the menin inhibitor administered without a CYP3A4 inhibitor. In some embodiments, the method increases the AUC of the menin inhibitor by about 2× to about 30× the AUC of the menin inhibitor administered without a CYP3A4 inhibitor. In some embodiments, the method increases the AUC of the menin inhibitor by about 2× to about 25× the AUC of the menin inhibitor administered without a CYP3A4 inhibitor. In some embodiments, the method increases the AUC of the menin inhibitor by about 2× to about 20× the AUC of the menin inhibitor administered without a CYP3A4 inhibitor. In some embodiments, the method increases the AUC of the menin inhibitor by about 2× to about 15× the AUC of the menin inhibitor administered without a CYP3A4 inhibitor. In some embodiments, the method increases the AUC of the menin inhibitor by about 2× to about 10× the AUC of the menin inhibitor administered without a CYP3A4 inhibitor. In some embodiments, the method method increases the AUC of the menin inhibitor by about 2× to about 5× the AUC of the menin inhibitor administered without a CYP3A4 inhibitor. In some embodiments, the method increases the AUC of the menin inhibitor by about 2× to about 4× the AUC of the menin inhibitor administered without a CYP3A4 inhibitor.

Disclosed herein, in certain embodiments, are methods of increasing the AUC of the menin inhibitor comprising administering a combination of the menin inhibitor and a CYP3A4 inhibitor. In some embodiments, the method increases the AUC of the menin inhibitor by about 15× to about 35× the AUC of the menin inhibitor administered without a CYP3A4 inhibitor, or about 20× to about 30×. In some embodiments, the method increases the AUC of the menin inhibitor by about 2× to about 35× the AUC of the menin inhibitor administered without a CYP3A4 inhibitor. In some embodiments, the method increases the AUC of the menin inhibitor by about 2× to about 30× the AUC of the menin inhibitor administered without a CYP3A4 inhibitor. In some embodiments, the method increases the AUC of the menin inhibitor by about 2× to about 25× the AUC of the menin inhibitor administered without a CYP3A4 inhibitor. In some embodiments, the method increases the AUC of the menin inhibitor by about 2× to about 20× the AUC of the menin inhibitor administered without a CYP3A4 inhibitor. In some embodiments, the method increases the AUC of the menin inhibitor by about 2× to about 15× the AUC of the menin inhibitor administered without a CYP3A4 inhibitor. In some embodiments, the method increases the AUC of the menin inhibitor by about 2× to about 10× the AUC of the menin inhibitor administered without a CYP3A4 inhibitor. In some embodiments, the method method increases the AUC of the menin inhibitor by about 2× to about 5× the AUC of the menin inhibitor administered without a CYP3A4 inhibitor. In some embodiments, the method increases the AUC of the menin inhibitor by about 2× to about 4× the AUC of the menin inhibitor administered without a CYP3A4 inhibitor. In some embodiments, the method increases the $C_{max}$ of the menin inhibitor. In some embodiments, $C_{max}$ of the menin inhibitor is increased by about 20× to about 40× the $C_{max}$ of the menin inhibitor administered without a CYP3A4 inhibitor, or about 25× to about 35×. In some embodiments, the method does not significantly affect the $T_{max}$ or $T_{1/2}$ of the menin inhibitor as compared to the $T_{max}$ and $T_{1/2}$ of the menin inhibitor administered without a CYP3A4 inhibitor.

Methods of Use

In some embodiments is a method of treating a cancer in an individual in need thereof comprising administering a combination of a menin inhibitor and a CYP3A4 inhibitor. Accordingly, the combinations and methods of the invention are believed to be effective against a broad range of cancers, including, but not limited to, hematological cancer (e.g., leukemia and lymphoma), bladder cancer, brain cancer (e.g., glioma, diffuse intrinsic pontine glioma (DIPG)), breast cancer (e.g., triple-negative breast cancer, estrogen-receptor-positive breast cancer (i.e., ER+ breast cancer)), colorectal cancer, cervical cancer, gastrointestinal cancer (e.g., colorectal carcinoma, gastric cancer), genitourinary cancer, head and neck cancer, liver cancer, lung cancer, melanoma, ovarian cancer, pancreatic cancer, prostate cancer (e.g., castration resistant prostate cancer), renal cancer (e.g., renal cell carcinoma), skin cancer, thyroid cancer (e.g., papillary thyroid carcinoma), testicular cancer, sarcoma (e.g., Ewing's sarcoma), and AIDS-related cancers. In some embodiments, the cancer is associated with a rearranged MLL gene. In some embodiments, the pathophysiology of the cancer is dependent on the MLL gene. In some embodiments, the MLL gene is M-LL1. In some embodiments, the cancer is associated with mutant p53 gain-of-function.

In some embodiments, the specific cancers that may be treated by the combinations, compositions and methods described herein include cardiac cancers, such as for example, sarcoma (e.g., angiosarcoma, fibrosarcoma, rhabdomyosarcoma, and liposarcoma), myxoma, rhabdomyoma, fibroma, lipoma and teratoma; lung cancers, including, for example, bronchogenic carcinoma (e.g., squamous cell, undifferentiated small cell, undifferentiated large cell, and adenocarcinoma), alveolar and bronchiolar carcinoma, bronchial adenoma, sarcoma, lymphoma, chondromatous hamartoma, mesothelioma, non-small cell lung cancer, small cell lung cancer, bronchial adenomas/carcinoids, and pleuropulmonary blastoma; gastrointestinal cancer, including, for example, cancers of the esophagus (e.g., squamous cell carcinoma, adenocarcinoma, leiomyosarcoma, and lymphoma), cancers of the stomach (e.g., carcinoma, lymphoma, and leiomyosarcoma), cancers of the pancreas (e.g., ductal adenocarcinoma, insulinoma, glucagonoma, gastrinoma, carcinoid tumors, and vipoma), cancers of the small bowel (e.g., adenocarcinoma, lymphoma, carcinoid tumors, Kaposi's sarcoma, leiomyoma, hemangioma, lipoma, neurofibroma, and fibroma), cancers of the large bowel or colon, (e.g., adenocarcinoma, tubular adenoma, villous adenoma, hamartoma, and leiomyoma), and other cancers of the digestive tract (e.g., anal cancer, anorectal cancer, appendix cancer, cancer of the anal canal, cancer of the tongue, gallbladder cancer, gastrointestinal stromal tumor (GIST), colon cancer, colorectal cancer, extrahepatic bile duct cancer, intrahepatic bile duct cancer, rectal cancer, and small intestine cancer); genitourinary tract cancers, including, for example, cancers of the kidney (e.g., adenocarcinoma, Wilm's tumor (nephroblastoma), lymphoma, and leukemia), cancers of the bladder and urethra (e.g., squamous cell carcinoma, transitional cell carcinoma, and adenocarcinoma), cancers of the prostate (e.g., adenocarcinoma and sarcoma), cancers of the testis, (e.g., seminoma, teratoma, embryonal carcinoma, teratocarcinoma, choriocarcinoma, sarcoma, interstitial cell carcinoma, fibroma, fibroadenoma, adenomatoid tumors, and lipoma), as well as transitional cell cancer, transitional cell cancer of the renal pelvis and ureter and other urinary organs, urethral cancer, and urinary bladder cancer; liver cancers, including, for example, hepatoma (e.g., hepatocellular carcinoma), cholangiocarcinoma, hepatoblastoma, angiosarcoma, hepatocellular adenoma, and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull (e.g., osteoma, hemangioma, granuloma, xanthoma, and osteitis deformans); cancers of the meninges (e.g., meningioma, meningiosarcoma, and gliomatosis); cancers of the brain (e.g., astrocytoma, medulloblastoma, glioma, ependymoma, germinoma (pinealoma), glioblastoma multiforme, oligodendroglioma, schwannoma, retinoblastoma, and congenital tumors); cancers of the spinal cord (e.g., neurofibroma, meningioma, glioma, and sarcoma), and other nervous system cancers (e.g., brain stem glioma, diffuse intrinsic pontine glioma (DIPG), brain tumor, central nervous system cancer, cerebellar astrocytoma, cerebral astrocytoma/malignant glioma, childhood cerebellar astrocytoma, childhood cerebral astrocytoma, primary central nervous system lymphoma, visual pathway and hypothalamic glioma, nervous system lymphoma, supratentorial primitive neuroectodeimal tumors, pineoblastoma and supratentorial primitive neuroectodermal tumors); gynecological cancers, including, for example, cancers of the uterus (e.g., endometrial carcinoma), cancers of the cervix (e.g., cervical carcinoma, and pre tumor cervical dysplasia), cancers of the ovaries (e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma), cancers of the vulva (e.g., squamous cell carcinoma, intraepithelial carcinoma, adenocarcinoma, fibrosarcoma, and melanoma), cancers of the vagina (e.g., clear cell carcinoma, squamous cell carcinoma, botryoid sarcoma, and embryonal rhabdomyosarcoma), and cancers of the fallopian tubes (e.g., carcinoma); other reproductive tract cancers, including, for example, endometrial cancer, endometrial uterine cancer, germ cell tumor, gestational trophoblastic tumor, gestational trophoblastic tumor glioma, ovarian epithelial cancer, ovarian germ cell tumor, ovarian low malignant potential tumor, penile cancer, vaginal cancer, vulvar cancer, extracranial germ cell tumor, extragonadal germ cell tumor, uterine cancer, uterine corpus cancer, uterine sarcoma; lymphatic and hematologic cancers, including, for example, cancers of the blood (e.g., acute myeloid leukemia (AML), chronic myeloid leukemia (CMIL), acute lymphoblastic leukemia (ALL), chronic lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia), and other lymphatic or hematologic cancers including, for example, childhood leukemia, myeloproliferative disorders (e.g., primary myelofibrosis), plasma cell neoplasm/multiple myeloma, myelodysplasia, myelodysplastic syndrome, cutaneous T-cell lymphoma, lymphoid neoplasm, AIDS-related lymphoma, thymoma, thymoma and thymic carcinoma, mycosis fungoides, and Sezary Syndrome; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis, merkel cell carcinoma, merkel cell skin carcinoma, melanoma, and carcinoid tumor; adrenal gland cancers, including, for example, neuroblastoma; other cancers associated with the endocrine system including, for example, adrenocortical carcinoma, multiple endocrine neoplasia (e.g., multiple endocrine neoplasia type I), multiple endocrine neoplasia syndrome, parathyroid cancer, pituitary tumor, pheochromocytoma, islet cell pancreatic cancer, and islet cell tumors); connective tissue cancer (e.g., bone cancer, bone and joint cancer, osteosarcoma and malignant fibrous histiocytoma); cancer associated with the head, neck, and mouth (e.g., head and neck cancer, paranasal sinus and nasal cavity cancer, metastatic squamous neck cancer, mouth cancer, throat cancer, esophageal cancer, laryngeal cancer, pharyngeal cancer, hypopharyngeal cancer, lip and oral cavity cancer, nasopharyngeal cancer, oral cancer, oropharyngeal cancer, and salivary gland cancer); and cancer associated with the eye (e.g., ocular cancer, intraocular melanoma). In some embodiments, the cancer is Ewing's sarcoma.

In some embodiments, the cancer is a hematological cancer such as leukemia or lymphoma. Example leukemia and lymphomas treatable by the compounds of the invention include mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL) (also referred to as acute lymphoblastic leukemia or acute lymphoid leukemia), acute myeloid leukemia (AML) (also referred to as acute myelogenous leukemia or acute myeloblastic leukemia), acute granulocytic leukemia, acute nonlymphocytic leukemia, chronic lymphocytic leukemia (CLL) (also referred to as chronic lymphoblastic leukemia), chronic myelogenous leukemia (CML) (also referred to as chronic myeloid leukemia), therapy related leukemia, myelodysplastic syndrome (MDS), myeloproliferative disease (MPD) (such as primary myelofibrosis (PMF)), myeloproliferative neoplasia (MPN), plasma cell neoplasm, multiple myeloma, myelodysplasia, cutaneous T-cell lymphoma, nucleophosmin (NPM1) AML, lymphoid neoplasm, AIDS-related lymphoma, thymoma, thymic carcinoma, mycosis fungoides, Alibert-Bazin syndrome, granuloma fungoides, Sezary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non Hodgkin's lymphoma (malignant lymphoma), and Waldenstrom's macroglobulinemia. In some embodiments, the acute myeloid leukemia (AML) is abstract nucleophosmin (NPM1)-mutated acute myeloid leukemia (i.e., NPM1" acute myloid leukemia).

In particular embodiments, compounds of the invention are used to treat leukemia associated with a MLL rearrangement, acute lymphocytic leukemia associated with a MLL rearrangement, acute lymphoblastic leukemia associated with a MLL rearrangement, acute lymphoid leukemia associated with a MLL rearrangement, acute myeloid leukemia associated with a MLL rearrangement, acute myelogenous leukemia associated with a MLL rearrangement, or acute myeloblastic leukemia associated with a MLL rearrangement. As used herein, "MLL rearrangement" means a rearrangement of the MLL gene.

In some embodiments, the CYP3A4 inhibitor is: an antiarrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A4 inhibitor is: alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfmavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; troleandromycin; verapamil; telaprevir; vincristine; voriconazole; or any combinations thereof. In some embodiments, the CYP3A4 inhibitor is cobicistat (GS-9350) or analogs or derivatives of cobicistat (GS-9350). In some embodiments, the CYP3A4 inhibitor is ketoconazole. In some embodiments, the CYP3A4 inhibitor is ritonavir.

In some embodiments, the method increases the $C_{max}$ of the menin inhibitor. In some embodiments, $C_{max}$ of the menin inhibitor is increased by about 20× to about 40× the $C_{max}$ of the menin inhibitor administered without a CYP3A4 inhibitor, or about 25× to about 35×. In some embodiments, the method increases the AUC of the menin inhibitor. In some embodiments, the method increases the AUC of the menin inhibitor by about 15× to about 35× the AUC of the menin inhibitor administered without a CYP3A4 inhibitor, or about 20× to about 30×. In some embodiments, the method increases the AUC of the menin inhibitor by about 2× to about 35× the AUC of the menin inhibitor administered without a CYP3A4 inhibitor. In some embodiments, the method increases the AUC of the menin inhibitor by about 2× to about 30× the AUC of the menin inhibitor administered without a CYP3A4 inhibitor. In some embodiments, the method increases the AUC of the menin inhibitor by about 2× to about 25× the AUC of the menin inhibitor administered without a CYP3A4 inhibitor. In some embodiments, the method increases the AUC of the menin inhibitor by about 2× to about 20× the AUC of the menin inhibitor administered without a CYP3A4 inhibitor. In some embodiments, the method increases the AUC of the menin inhibitor by about 2× to about 15× the AUC of the menin inhibitor administered without a CYP3A4 inhibitor. In some embodiments, the method increases the AUC of the menin inhibitor by about 2× to about 10× the AUC of the menin inhibitor administered without a CYP3A4 inhibitor. In some embodiments, the method method increases the AUC of the menin inhibitor by about 2× to about 5× the AUC of the menin inhibitor administered without a CYP3A4 inhibitor. In some embodiments, the method increases the AUC of the menin inhibitor by about 2× to about 4× the AUC of the menin inhibitor administered without a CYP3A4 inhibitor. In some embodiments, the method does not significantly affect the $T_{max}$ or $T_{1/2}$ of the menin inhibitor as compared to the $T_{max}$ and $T_{1/2}$ of the menin inhibitor administered without a CYP3A4 inhibitor. In some embodiments, the menin inhibitor and the CYP3A4 inhibitor are in a combined dosage form. In some embodiments, the menin inhibitor and the CYP3A4 inhibitor are in separate dosage forms. In some embodiments, the menin inhibitor and the CYP3A4 inhibitor are administered concurrently. In some embodiments, the menin inhibitor and the CYP3A4 inhibitor are administered simultaneously, essentially simultaneously or within the same treatment protocol. In some embodiments, the menin inhibitor and the CYP3A4 inhibitor are administered sequentially. In some embodiments, the methods further comprise co-administering chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the methods further comprise co-administering cyclophosphamide, hydroxydaunorubicin, vincristine, and prednisone, and optionally, rituximab. In some embodiments, the methods further comprise co-administering bendamustine, and rituximab. In some embodiments, the methods further comprise co-administering fludarabine, cyclophosphamide, and rituximab. In some embodiments, the methods further comprise coadministering cyclophosphamide, vincristine, and prednisone, and optionally, rituximab. In some embodiments, the methods further comprise co-administering etoposide, doxorubicin, vincristine, cyclophosphamide, prednisolone, and optionally, rituximab. In some embodiments, the methods further comprise co-administering dexamethasone and lenalidomide. In some embodiments, the menin inhibitor is amorphous or crystalline.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B. C. Decker Inc., Hamilton, Ontario, 2003).

The present combination is additionally useful for the treatment of leukemia patients with an MLL/KMT2A gene rearrangement.

Leukemia

Disclosed herein, in certain embodiments, is a method for treating a leukemia in an individual in need thereof, comprising: administering a menin inhibitor a CYP3A4 inhibitor. Disclosed herein, in some embodiments, is a method for treating a leukemia in an individual in need thereof, comprising: administering a menin inhibitor and administering a CYP3A4 inhibitor. Further disclosed herein, in certain embodiments, is a method for treating a leukemia in an individual in need thereof, comprising: administering a pharmaceutical composition comprising a menin inhibitor and a CYP3A4 inhibitor. In some embodiments disclosed herein is a method for treating a leukemia in an individual in need thereof, comprising: administering a pharmaceutical composition comprising a menin inhibitor and a pharmaceutical composition comprising a CYP3A4 inhibitor.

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), Acute myelogenous leukemia (AML), Chronic myelogenous leukemia (CML), and Hairy cell leukemia (HCL).

Symptoms, diagnostic tests, and prognostic tests for each of the above-mentioned conditions are known. See, e.g., Harrison's Principles of Internal Medicine© " 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of inhibitor compounds, such as the menin inhibitor, for treating any of the foregoing diseases.

The therapeutic efficacy of menin inhibitor for any one of the foregoing diseases can be optimized during a course of treatment. For example, a subject being treated can undergo a diagnostic evaluation to correlate the relief of disease symptoms or pathologies to inhibition of in vivo menin activity achieved by administering a given dose of the menin inhibitor. Cellular assays known in the art can be used to determine in vivo activity. Thus, the amount of the menin inhibitor compound that is administered to a subject can be increased or decreased as needed so as to maintain a level of menin inhibition optimal for treating the subject's disease state.

In some embodiments, a menin inhibitor and a CYP3A4 inhibitor are used for the manufacture of a medicament for treating any of the foregoing conditions. In some embodiments, the combination of the present invention is directed to the treatment of leukemia. In some embodiments, the present invention is directed to the treatment of leukemia in a patient in need thereof comprising administering a menin inhibitor and a CYP3A4 inhibitor. In some further embodiments, the present invention is directed to the treatment of leukemia in a patient in need thereof comprising administering a pharmaceutical composition comprising a menin inhibitor and a pharmaceutical composition comprising a CYP3A4 inhibitor. In some further embodiments, the present invention is directed to the treatment of leukemia in a patient in need thereof comprising administering a pharmaceutical composition comprising a menin inhibitor of Formula I and a pharmaceutical composition comprising a azole antifungal CYP3A4 inhibitor.

Acute leukemias generally result from acquired mutations in hematopoietic progenitor cells. Chromosomal abnormalities are often discrete mutational features in leukemia. Many of these chromosomal abnormalities are due to specific translocations that lead to the formation of fusion genes which become drivers for tumorigenesis and tumor development. A specific example involves the MLL1 gene. Translocations at the MLL1 locus (11q23) can lead to the formation of oncogenic gene fusions that characterize MLLr acute leukemias. The MLL1 protein is a key regulator of development and is the mammalian homologue of *Drosophila* trithorax. It is an important epigenetic regulator of HOX gene expression. Translocations at the MLL1 locus create chimeric proteins that fuse the N-terminus of MLL1 to variable C-terminal domains derived from different translocation partners. Currently, more than 90 different fusion partners are known. Expression of these fusions enables an aberrant transcription program characterized by overexpression of HOX and other developmental genes. This transcription program suppresses differentiation and enhances proliferation, leading to the MLLr acute leukemias. Translocations involving the MLL1 locus (11q23) are routinely diagnosed using fluorescence in situ hybridization (FISH). Depending on the progenitor cell of origin, MLLr can phenotypically appear as ALL, AML, or mixed phenotype acute leukemia (MPAL). These translocations are rare and MLLr has a combined annual incidence of ~4000 cases per year in the United States (US), Europe and Japan. Approximately 10% of all leukemias harbor MLL1 translocations.

The present combination is additionally useful for the treatment of leukemia patients with an MLL/KMT2A gene rearrangement.

The relapse risk for MLLr patients is high after conventional chemotherapy and stem cell transplantation, with an overall 5-year survival rate of only approximately 35%. No therapies are currently available that specifically target MLLr leukemia. The menin inhibitors of Formula I or Formula II in combination with a CYP3A4 inhibitor may provide a novel, targeted treatment for MLLr acute leukemias.

Treatment of Relapsed or Refractory MLLr Acute Leukemias

The interaction of MLL1 fusion proteins with menin is a key driver of MLLr acute leukemias. Both MLL1 and MLLr fusions bind to a well-characterized high affinity site on the chromatin-associated protein menin. The binding of MLL1 fusions to menin is mediated by amino acid residues 9-13 (FPARP) found at the N-terminus of MHLL1. Binding to menin localizes these fusions to chromatin where they enable a leukemic transcription program, which includes upregulation of HOXA locus and MEIS1 genes. The interaction between the fusion protein and menin is required to maintain this transcription program.

The menin inhibitors of Formula I or Formula II binds with high affinity to the MLL1 binding pocket on menin and displays activity across a range of cells harboring MLLr fusions. Menin inhibitors of Formula I or Formula II disrupts the interaction between menin and the MLL1 fusion proteins which is required for leukemogenic activity, thus impairing expression of critical oncogenes, causing growth arrest and the inhibition of cellular proliferation. Small molecule inhibitors of the menin-VLL interaction have been reported. These inhibitors have demonstrated anti-proliferative activity against MLLr cell lines and have shown single agent survival benefit in mouse models of MLLr leukemia.

Similarly, combining menin inhibitors of Formula I or Formula II in with a CYP3A4 inhibitor increases efficacy and has demonstrated robust activity in multiple leukemic xenograft models and provided profound survival benefit after oral dosing in nonclinical models. Overall, these data indicate that pharmacologic inhibition of the menin-MLL interaction represents a potential targeted strategy for the treatment MLLr acute leukemias.

NPM1c AML

AML is an acute leukemia characterized by accumulation of myeloid cells in the bone marrow as a result of impaired differentiation and proliferation. NPM1 is among the most frequently mutated genes in AML. Point mutations in the NPM1 gene lead to the aberrant cytoplasmic localization of the mutant proteins, which are termed NPM1c. The identification of NPM1c is an essential part of the diagnostic screening of AML. AML patients with mutations in NPM1 alone have a favorable prognosis with ~60% five-year overall survival (OS). However, most (>80%) NPM1c AML patients harbor multiple concurrent mutations which can adversely affect the prognosis. Co-mutations have been found in FLT3, DNMT3A, NRAS, TET2 and IDH1/2 genes, among others. NPM1c is generally not found in ALL.

The American Cancer Society estimates there will be ~21,450 new cases of AML in the US in 2019. In adult AML, ~30% of patients have NPM1c. Given the findings that NPM1c harboring cells are very sensitive to menin-MLL interaction inhibitors, the menin inhibitors of Formula I or Formula II in combination with a CYP3A4 inhibitor may provide a novel, targeted treatment for NPM1c AML.

Treatment of Patients with NPM1c AML

NPM1 normally exists as a nucleolar protein that shuttles between the nucleus and cytoplasm. It has multiple functions, including ribosomal protein assembly and transport, control of centrosome duplication, and regulation of the tumor suppressor ARF. The cytosolic localization of mutant NPM1c leads to the aberrant partitioning of NPM1c-associated nuclear proteins into the cytoplasm, including several transcription factors. Among these is PU.1, a master driver of monocyte lineage differentiation. Loss of PU.1 from the nucleus in NPM1c AML leads to suppression of >500 terminal differentiation genes. The suppression of differentiation by NPM1c enables a leukemic transcription program that is highly dependent on the up-regulated expression of HOXA cluster and MEISI genes. Expression of these genes further blocks differentiation and induces long-term proliferation, leading to the leukemic phenotype.

In addition, the HOX/MEIS signatures of NPM1c AMLs overlap with those of MLLr leukemias and hematopoietic stem cells (HSC). Maintenance of this transcription signature in NPM1c cells depends directly on the menin-MLL1 interaction.

While little is known regarding how mutant NPM1c cells maintain aberrant gene expression, mutation of the menin binding motif in MLL1 has been shown to strongly inhibit the proliferative capacity of NPM1c cells due to loss of MLL1 binding to menin. In addition, the small molecule menin-MLL interaction inhibitor, MI-503, was shown to suppress the HOXA MEIS1 transcription program in NPM1c cells, leading to growth arrest, terminal differentiation and cell death, confirming a critical role for the menin-MLL1 interaction in NPM1c cells. These findings were validated and extended in another report that demonstrated that the orally active menin inhibitor, KO-539, had robust anti-leukemic activity in NPM1c mutant AML patient-derived xenograft models. Overall, these results demonstrated that NPM1c harboring cells are very sensitive to menin-MLL interaction inhibitors.

In some embodiments, the combination of the present invention is directed to the treatment of NMP1 AML. In some embodiments, the present invention is directed to the treatment of NMP1 AML in a patient in need thereof comprising administering a menin inhibitor and a CYP3A4 inhibitor. In some further embodiments, the present invention is directed to the treatment of NMP1 AML in a patient in need thereof comprising administering a pharmaceutical composition comprising a menin inhibitor and a pharmaceutical composition comprising a CYP3A4 inhibitor. In some further embodiments, the present invention is directed to the treatment of NMP1 AML in a patient in need thereof comprising administering a pharmaceutical composition comprising a menin inhibitor of Formula I and a pharmaceutical composition comprising a azole antifungal CYP3A4 inhibitor.

Additional Combination Therapies

In certain instances, it is appropriate to administer a menin inhibitor and a CYP3A4 inhibitor in combination with an additional therapeutic agent. In certain instances, it is appropriate to administer the menin inhibitor and a CYP3A4 inhibitor in combination with an additional CYP3A4 inhibitor. Additional therapeutic agents are selected for their particular usefulness against the condition that is being treated. In general, the additional therapeutic agent does not need to be administered in the same pharmaceutical composition, at the same time or via the same route and the menin inhibitor and/or CYP3A4 inhibitor. In some embodiments, the initial administration is made according to established protocols, and then, based upon the observed effects, the dosage, modes of administration and times of administration are further modified.

In some embodiments, the additional therapeutic agent is administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

The dose of the additional therapeutic agent varies depending on the additional therapeutic agent, the disease or condition being treated and so forth.

Disclosed herein, in certain embodiments, are methods of treating an autoimmune disorder, a heteroimmune disorder, an inflammatory disorder and/or a cancer in an individual in need thereof, comprising administering to the individual a menin inhibitor, a CYP3A4 inhibitor, and an additional therapeutic agent. Further disclosed herein, in certain embodiments, are methods of treating an autoimmune disorder in an individual in need thereof, comprising administering to the individual a menin inhibitor, a CYP3A4 inhibitor, and an additional therapeutic agent. Also disclosed herein, in certain embodiments, are methods of treating a heteroimmune disorder in an individual in need thereof comprising administering to the individual a menin inhibitor, a CYP3A4 inhibitor, and an additional therapeutic agent. Disclosed herein, in certain embodiments, are methods of treating an inflammatory disorder in an individual in need thereof, comprising administering to the individual a menin inhibitor, a CYP3A4 inhibitor, and an additional therapeutic agent. Further disclosed herein, in certain embodiments, are methods of treating a cancer in an individual in need thereof, comprising administering to the individual a menin inhibitor, a CYP3A4 inhibitor, and an additional therapeutic agent.

Disclosed herein, in certain embodiments, are methods of treating an autoimmune disorder, a heteroimmune disorder, an inflammatory disorder and/or a cancer in an individual in need thereof, comprising administering to the individual the menin inhibitor, a CYP3A4 inhibitor, and an additional therapeutic agent. Further disclosed herein, in certain embodiments, are methods of treating an autoimmune disorder in an individual in need thereof, comprising administering to the individual the menin inhibitor, a CYP3A4 inhibitor, and an additional therapeutic agent. Also disclosed herein, in certain embodiments, are methods of treating a heteroimmune disorder in an individual in need thereof comprising administering to the individual the menin inhibitor, a CYP3A4 inhibitor, and an additional therapeutic agent. Disclosed herein, in certain embodiments, are methods of treating an inflammatory disorder in an individual in need thereof, comprising administering to the individual the menin inhibitor, a CYP3A4 inhibitor, and an additional therapeutic agent. Further disclosed herein, in certain embodiments, are methods of treating a cancer in an individual in need thereof, comprising administering to the individual the menin inhibitor, a CYP3A4 inhibitor, and an additional therapeutic agent.

In some embodiments, administering a menin inhibitor before a second cancer treatment regimen reduces immune-mediated reactions to the second cancer treatment regimen.

In some embodiments, administering the menin inhibitor before ofatumumab reduces immune-mediated reactions to ofatumumab.

In some embodiments, the additional therapeutic agent is a chemotherapeutic agent, a steroid, an immunotherapeutic agent, a targeted therapy, or a combination thereof. In some embodiments, the additional therapeutic agent is a CD79A inhibitor, a CD79B inhibitor, a CD 19 inhibitor, a Lyn inhibitor, a Syk inhibitor, a PI3K inhibitor, a Blnk inhibitor, a PLCy inhibitor, a PKCP inhibitor, or a combination thereof. In some embodiments, the additional therapeutic agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a $Jak_{1/2}$ inhibitor, a protease inhibitor, a PKC inhibitor, a PARP inhibitor, or a combination thereof.

In some embodiments, the additional therapeutic agent is chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In some embodiments, the additional therapeutic agent is cyclophosphamide, hydroxydaunorubicin, vincristine, and prednisone, and optionally, rituximab. In some embodiments, the additional therapeutic agent is bendamustine, and rituximab. In some embodiments, the additional therapeutic agent is fludarabine, cyclophosphamide, and rituximab. In some embodiments, the additional therapeutic agent is cyclophosphamide, vincristine, and prednisone, and optionally, rituximab. In some embodiments, the additional therapeutic agent is etoposide, doxorubicin, vincristine, cyclophosphamide, prednisolone, and optionally, rituximab. In some embodiments, the additional therapeutic agent is dexamethasone and lenalidomide.

Additional therapeutic agents that maybe administered in conjunction with the combination of the menin inhibitor and a CYP3A4 inhibitor include, but are not limited to, Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; *Vinca* Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfm; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

Further therapeutic agents that maybe administered in conjunction with the combination of the menin inhibitor and a CYP3A4 inhibitor include, but are not limited to interferons, interleukins, Tumor Necrosis Factors, Growth Factors, or the like.

Additional therapeutic agents that maybe administered in conjunction with the combination of the menin inhibitor and a CYP3A4 inhibitor include, but are not limited to, Immunostimulants such as for example ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

Further therapeutic agents that maybe administered in conjunction with the combination of the menin inhibitor and a CYP3A4 inhibitor include, but are not limited to, Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Additional therapeutic agents that maybe administered in conjunction with the combination of the menin inhibitor and a CYP3A4 inhibitor include, but are not limited to, Monoclonal Antibodies such as for example alemtuzumab, bevacizumab, catumaxomab, cetuximab, edrecolomab, gemtuzumab, ofatumumab, panitumumab, rituximab, trastuzumab, Immunosuppressants, eculizumab, efalizumab, muromab-CD3, natalizumab; TNF alpha Inhibitors such as for example adalimumab, afelimomab, certolizumab pegol, golimumab, infliximab, Interleukin Inhibitors, basiliximab, canakinumab, daclizumab, mepolizumab, tocilizumab, ustekinumab, Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

Further therapeutic agents that maybe administered in conjunction with the combination of the menin inhibitor and a CYP3A4 inhibitor include, but are not limited to, agents that affect the tumor micro-environment such as cellular signaling network (e.g. phosphatidylinositol 3-kinase (PI3K) signaling pathway, signaling from the B-cell receptor and the IgE receptor). In some embodiments, the second agent is a PI3K signaling inhibitor or a syc kinase inhibitor. In some embodiments, the syk inhibitor is R788. In another embodiment, the second agent is a PKCy inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, B16727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, PF-00562271, PF-02341066, PF-03814735, PF-04217903, PF-04554878, PF-04691502, PF-3758309, PHA-739358, PLC3397, progenipoietin, R547, R763, ramucirumab, regorafenib, R05185426, SAR103168, SCH 727965, SGI-1176, SGX523, SNS-314, TAK-593, TAK-901, TK1258, TLN-232, TTP607, XL147, XL228, XL281R05126766, XL418, XL765.

Further examples of therapeutic agents for use in combination with the menin inhibitor and a CYP3A4 inhibitor include, but are not limited to, inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other agents that may be employed in combination with the menin inhibitor and a CYP3A4 inhibitor include, but are not limited to, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; chlorambucil; cirolemycin; cladribine; crisnatol mesylate; cyclophosphamide; cytarabine; dacarbazine; daunorubicin hydrochloride; decitabine; dexormap latin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fiudarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rlL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safmgol; safmgol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfm; teniposide; teroxirone; testolactone; thiamiprine; thioguanine; thiotepa; tiazofurin; tirapazamine;

toremifene citrate; trestolone acetate; triciribine phosphate; trimetrexate; trimetrexate glucuronate; triptorelin; tubulozole hydrochloride; uracil mustard; uredepa; vapreotide; verteporfm; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further therapeutic agents that maybe administered in conjunction with the combination of the menin inhibitor and a CYP3A4 inhibitor include, but are not limited to, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixImab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safmgol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfm; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors;

ubenimex; urogenital sinus-derived growth inhibitory factor; urokinase receptor antagonists; vapreotide; variolin B; vector system, erythrocyte gene therapy; velaresol; veramine; verdins; verteporfm; vinorelbine; vinxaltine; vitaxin; vorozole; zanoterone; zeniplatin; zilascorb; and zinostatin stimalamer.

Other therapeutic agents that maybe administered in conjunction with the combination of the menin inhibitor and a CYP3A4 inhibitor include, but are not limited to, another CYP3A4 inhibitor, alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analogs (e.g., methotrexate), or pyrimidine analogs (e.g., Cytarabine), purine analogs (e.g., mercaptopurine, thioguanine, pentostatin).

Examples of alkylating agents that include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Additional therapeutic agents that maybe administered in conjunction with the combination of the menin inhibitor and a CYP3A4 inhibitor include, but are not limited to: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta *Medica*), D-68836 (Asta *Medica*), Myoseverin B, D-43411 (Zentaris, also known as D-81862), A-289099 (Abbott), A-318315 (Abbott), HTI-286 (also known as SPA-110, trifiuoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

The menin inhibitor and a CYP3A4 inhibitor may be used in combination with: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofm, sulfasalazine, hydroxychloroquinine, minocycline, TNF-α binding proteins (e.g., infliximab, etanercept, or adalimumab), abatacept, anakinra, interferon-3, interferon-7, interleukin-2, allergy vaccines, antihistamines, antileukotrienes, beta-agonists, theophylline, or anticholinergics.

Pharmaceutical Compositions/Formulations

Disclosed herein, in certain embodiments, are pharmaceutical compositions comprising a menin inhibitor and a pharmaceutically-acceptable excipient and pharmaceutical compositions CYP3A4 inhibitor and a pharmaceutically-acceptable excipient. Further disclosed herein, in certain embodiments, are pharmaceutical compositions comprising (a) the menin inhibitor and a CYP3A4 inhibitor, and (b) a pharmaceutically-acceptable excipient.

In some embodiments, the CYP3A4 inhibitor is: an anti-arrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A4 inhibitor is: posaconazole; conivaptan; lopinavir; alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS- 9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfmavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; verapamil; telaprevir; vincristine; voriconazole; or any combinations thereof.

In some embodiments, the CYP3A4 inhibitor is posaconazole. In some embodiments, the CYP3A4 inhibitor is cobicistat (GS-9350) or analogs or derivatives of cobicistat (GS-9350). In some embodiments, the CYP3A4 inhibitor is ketoconazole. In some embodiments, the CYP3A4 inhibitor is ritonavir. In some embodiments, the CYP3A4 inhibitor is conivaptan. In some embodiments, the CYP3A4 inhibitor is lopinavir.

In some embodiments, the menin inhibitor is amorphous or crystalline. In some embodiments, the menin inhibitor is milled or a nano-particle. In some embodiments, the pharmaceutical composition is a combined dosage form. In some embodiments, the composition increases the oral bioavailability of the menin inhibitor. In some embodiments, the composition increases the $C_{max}$ of the menin inhibitor. In some embodiments, the composition increases the AUC of the menin inhibitor. In some embodiments, the composition increases the $C_{max}$ of the menin inhibitor by about 20× to about 40× the $C_{max}$ of the menin inhibitor administered without a CYP3A4 inhibitor, or about 25× to about 35×. In some embodiments, the composition increases the AUC of the menin inhibitor by about 15× to about 35× the AUC of the menin inhibitor administered without a CYP3A4 inhibitor, or about 20× to about 30×. In some embodiments, the composition comprises an amount of the CYP3A4 inhibitor that is effective to increase the AUC of the menin inhibitor by about 2× to about 35× the AUC of the menin inhibitor administered without a CYP3A4 inhibitor. In some embodiments, the composition comprises an amount of the CYP3A4 inhibitor that is effective to increase the AUC of the menin inhibitor by about 2× to about 30× the AUC of the menin inhibitor administered without a CYP3A4 inhibitor. In some embodiments, the composition comprises an amount of the CYP3A4 inhibitor that is effective to increase the AUC of the menin inhibitor by about 2× to about 25× the AUC of the menin inhibitor administered without a C YP3A4 inhibitor. In some embodiments, the composition comprises an amount of the CYP3A4 inhibitor that is effective to increase the AUC of the menin inhibitor by about 2× to about 20× the AUC of the menin inhibitor administered without a CYP3A4 inhibitor. In some embodiments, the composition comprises an amount of the CYP3A4 inhibitor that is effective to increase the AUC of the menin inhibitor by about 2× to about 15× the AUC of the menin inhibitor administered without a CYP3A4 inhibitor. In some embodiments, the composition comprises an amount of the CYP3A4 inhibitor that is effective to increase the AUC of the menin inhibitor by about 2× to about 10× the AUC of the menin inhibitor administered without a CYP3A4 inhibitor. In some embodiments, the composition comprises an amount of the CYP3A4 inhibitor that is effective to increase the AUC of the menin inhibitor by about 2× to about 5× the AUC of the menin inhibitor administered without a CYP3A4 inhibitor. In some embodiments, the composition comprises an amount of the CYP3A4 inhibitor that is effective to increase the AUC of the menin inhibitor by about 2× to about 4× the AUC of the menin inhibitor administered without a CYP3A4 inhibitor. In some embodiments, the composition does not significantly affect the $T_{max}$ or T ½ of the menin inhibitor as compared to the $T_{max}$ and $T_{1/2}$ of the menin inhibitor administered without a CYP3A4 inhibitor.

In some embodiments, the pharmaceutical compositions further comprise chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the pharmaceutical compositions further comprise cyclophosphamide, hydroxydaunorubicin, vincristine, and prednisone, and optionally, rituximab. In some embodiments, the pharmaceutical compositions further comprise bendamustine, and rituximab. In some embodiments, the pharmaceutical compositions further comprise fludarabine, cyclophosphamide, and rituximab. In some embodiments, the pharmaceutical compositions further comprise cyclophosphamide, vincristine, and prednisone, and optionally, rituximab. In some embodiments, the pharmaceutical compositions further comprise etoposide, doxorubicin, vincristine, cyclophosphamide, prednisolone, and optionally, rituximab. In some embodiments, the pharmaceutical compositions further comprise dexamethasone and lenalidomide.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference in their entirety.

A pharmaceutical composition, as used herein, refers to a mixture of the menin inhibitor, a CYP3A4 inhibitor, and/or an additional therapeutic agent with other chemical components, such as carriers, stabilizers, diluents, dispersing agents, suspending agents, thickening agents, and/or excipients.

In practicing the methods of treatment or use provided herein, therapeutically effective amounts of the compounds disclosed herein are administered having a disease, disorder, or condition to be treated. In some embodiments, the mammal is a human. The therapeutically effective amounts of the compounds may vary depending on the compounds, severity of the disease, the age and relative health of the subject, and other factors.

The term "combination" as used herein, means a product that results from the mixing or combining of the menin inhibitor and a CYP3A4 inhibitor (and any additional therapeutic agents) and includes both fixed and non-fixed combinations. The term "fixed combination" means that the menin inhibitor and the CYP3A4 inhibitor are both administered in a single entity or dosage form. The term "non-fixed combination" means that the menin inhibitor and the CYP3A4 inhibitor are administered as separate entities or dosage forms either simultaneously, concurrently or sequentially with no specific intervening time limits, wherein such administration provides effective levels of the two compounds in the body of the patient. The latter also applies to cocktail therapy, e.g. the administration of three or more active ingredients.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

Disclosed herein, in certain embodiments, are one or more dosage forms or pharmaceutical compositions comprising a menin inhibitor administered in combination with one or more dosage forms or pharmaceutical compositions comprising a CYP3A4 inhibitor.

The pharmaceutical compositions of the present application comprise a therapeutically effective amount of a compound (e.g. the menin inhibitor, the CYP3A4 inhibitor or both) of the present application formulated together with one or more pharmaceutically acceptable carriers. Compounds of the application may be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including the individual compounds of the combination of the present application in free form or in a pharmaceutically acceptable salt form in association with at least one pharmaceutically acceptable carrier or diluent may be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier may include absorbable pharmacologically acceptable solvents to assist passage through the skin of the host. For example, transdermal devices may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives. The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracisternally, intravaginally, intraperitoneally, topically (as by powders, ointments, or drops), buccally, or as an oral or nasal spray.

As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracisternally, intravaginally, intraperitoneally, topically (as by powders, ointments, or drops), buccally, or as an oral or nasal spray.

Liquid dosage forms for oral administration may include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Further disclosed herein, in some embodiments, are dosage forms comprising the menin inhibitor and a CYP3A4 inhibitor. In some embodiments, the dosage form is a combined dosage form. In some embodiments, the dosage form is a solid oral dosage form. In some embodiments, the dosage form is a tablet, pill, or capsule. In some embodiments, the dosage form is a controlled release dosage form, delayed release dosage form, extended release dosage form, pulsatile release dosage form, multiparticulate dosage form, or mixed immediate release and controlled release formulation. In some embodiments, the dosage form comprises a controlled release coating. In some embodiments, the dosage forms comprise a first controlled release coating which controls the release of the menin inhibitor and a second controlled release coating which controls the release of the CYP3A4 inhibitor.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the CYP3A4 inhibitor is: an antiarrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A4 inhibitor is: alprazolam;

amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfinavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; troleandromycin, verapamil; telaprevir; vincristine; voriconazole; or any combinations thereof. In some embodiments, the CYP3A4 inhibitor is cobicistat (GS-9350) or analogs or derivatives of cobicistat (GS-9350). In some embodiments, the CYP3A4 inhibitor is ketoconazole. In some embodiments, the CYP3A4 inhibitor is ritonavir.

In some embodiments, the menin inhibitor is amorphous or crystalline. In some embodiments, the dosage form increases the oral bioavailability of the menin inhibitor. In some embodiments, the dosage form increases the $C_{max}$ of the menin inhibitor. In some embodiments, the dosage form increases the AUC of the menin inhibitor. In some embodiments, the dosage form increases the $C_{max}$ of the menin inhibitor by about 20× to about 40× the $C_{max}$ of the menin inhibitor administered without a CYP3A4 inhibitor, or about 25× to about 35×. In some embodiments, the dosage form increases the AUC of the menin inhibitor by about 15× to about 35× the AUC of the menin inhibitor administered without a CYP3A4 inhibitor, or about 20× to about 30×. In some embodiments, the dosage form increases the AUC of the menin inhibitor by about 2× to about 35× the AUC of the menin inhibitor administered without a CYP3A4 inhibitor. In some embodiments, the dosage form increases the AUC of the menin inhibitor by about 2× to about 30× the AUC of the menin inhibitor administered without a CYP3A4 inhibitor. In some embodiments, the dosage form increases the AUC of the menin inhibitor by about 2× to about 25× the AUC of the menin inhibitor administered without a CYP3A4 inhibitor. In some embodiments, the dosage form increases the AUC of the menin inhibitor by about 2× to about 20× the AUC of the menin inhibitor administered without a CYP3A4 inhibitor. In some embodiments, the dosage form increases the AUC of the menin inhibitor by about 2× to about 15× the AUC of the menin inhibitor administered without a CYP3A4 inhibitor. In some embodiments, the dosage form increases the AUC of the menin inhibitor by about 2× to about 10× the AUC of the menin inhibitor administered without a CYP3A4 inhibitor. In some embodiments, the dosage form increases the AUC of the menin inhibitor by about 2× to about 5× the AUC of the menin inhibitor administered without a CYP3A4 inhibitor. In some embodiments, the dosage form increases the AUC of the menin inhibitor by about 2× to about 4× the AUC of the menin inhibitor administered without a CYP3A4 inhibitor. In some embodiments, the dosage form does not significantly affect the $T_{max}$ or $T_{1/2}$ of the menin inhibitor as compared to the $T_{max}$ and $T_{1/2}$ of the menin inhibitor administered without a CYP3A4 inhibitor. In some embodiments, the dosage forms further comprise chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the dosage forms further comprise cyclophosphamide, hydroxydaunorubicin, vincristine, and prednisone, and optionally, rituximab. In some embodiments, the dosage forms further comprise bendamustine, and rituximab. In some embodiments, the dosage forms further comprise fludarabine, cyclophosphamide, and rituximab. In some embodiments, the dosage forms further comprise cyclophosphamide, vincristine, and prednisone, and optionally, rituximab. In some embodiments, the dosage forms further comprise etoposide, doxorubicin, vincristine, cyclophosphamide, prednisolone, and optionally, rituximab. In some embodiments, the dosage forms further comprise dexamethasone and lenalidomide.

The pharmaceutical compositions described herein may be formulated for administration via any conventional means including, but not limited to, oral, parenteral (e.g., intravenous, subcutaneous, or intramuscular), buccal, intranasal, rectal or transdermal administration routes. As used herein, the terms “subject”, “individual” and “patient” are used interchangeably and mean an animal, preferably a mammal, including a human or non-human. None of the terms require the supervision (continuous or otherwise) of a medical professional.

The pharmaceutical compositions described herein are formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al, The Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

The pharmaceutical dosage forms described herein may include one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington’s Pharmaceutical Sciences, 20th Edition (2000), a film coating is provided around the pharmaceutical compositions. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In some embodiments, the active compound is mixed under sterile conditions with a pharmaceutically acceptable carrier, and with any preservatives, buffers or propellants that are required.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Techniques for formulation and administration of the disclosed compounds of the application can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Dosing and Treatment Regimens

In some embodiments, the amount of the menin inhibitor that is administered in combination with a CYP3A4 inhibitor is from 50 mg/day up to, and including, 1000 mg/day.

In some embodiments, the daily dosage of the menin inhibitor is between about 10 mg to about 500 mg. In some embodiments, the daily dosage of the menin inhibitor is between about 200 mg and about 500 mg. In some embodiments, the daily dosage of the menin inhibitor is between about 250 mg and about 460 mg. In some embodiments, the daily dosage amount of the menin inhibitor is about 226 mg. In some embodiments, the daily dosage of the menin inhibitor is 452 mg.

In some embodiments, a dose is given once a day, given twice a day, given three times per day, given four times per day to equal the daily dose. In some embodiments, the menin inhibitor is administered at a unit dose of 113 mg. In some embodiments, the unit dose is given once a day, given twice a day, given three times per day, given four times per day. In some embodiments, one unit dose is given per day, two unit doses are given per day, three unit doses are given per day, four unit doses are given per day. In some embodiments, two unit doses are given twice per day.

In some embodiments, the amount of the menin inhibitor that is administered is about 40 mg/day. In some embodiments, the amount of the menin inhibitor that is administered is about 50 mg/day. In some embodiments, the amount of the menin inhibitor that is administered is about 60 mg/day. In some embodiments, the amount of the menin inhibitor that is administered is about 70 mg/day. In some embodiments, the amount of the menin inhibitor that is administered is about 80 mg/day. In some embodiments, the amount of the menin inhibitor that is administered is about 90 mg/day. In some embodiments, the amount of the menin inhibitor that is administered is about 100 mg/day. In some embodiments, the amount of the menin inhibitor that is administered is about 110 mg/day. In some embodiments, the amount of the menin inhibitor that is administered is about 120 mg/day. In some embodiments, the amount of the menin inhibitor that is administered is about 130 mg/day. In some embodiments, the amount of the menin inhibitor that is administered is about 140 mg/day. In some embodiments, the amount of the menin inhibitor that is administered is about 150 mg/day. In some embodiments, the amount of the menin inhibitor that is administered is about 160 mg/day. In some embodiments, the amount of the menin inhibitor that is administered is about 170 mg/day. In some embodiments, the amount of the menin inhibitor that is administered is about 180 mg/day. In some embodiments, the amount of the menin inhibitor that is administered is about 190 mg/day. In some embodiments, the amount of the menin inhibitor that is administered is about 200 mg/day. In some embodiments, the amount of the menin inhibitor that is administered is about 210 mg/day. In some embodiments, the amount of the menin inhibitor that is administered is about 220 mg/day. In some embodiments, the amount of the menin inhibitor that is administered is about 230 mg/day. In some embodiments, the amount of the menin inhibitor that is administered is about 240 mg/day. In some embodiments, the amount of the menin inhibitor that is administered is about 250 mg/day. In some embodiments, the amount of the menin inhibitor that is administered is about 260 mg/day. In some embodiments, the amount of the menin inhibitor that is administered is about 270 mg/day. In some embodiments, the amount of the menin inhibitor that is administered is about 280 mg/day. In some embodiments, the amount of the menin inhibitor that is administered is about 290 mg/day. In some embodiments, the amount of the menin inhibitor that is administered is about 300 mg/day. In some embodiments, the amount of the menin inhibitor that is administered is about 310 mg/day. In some embodiments, the amount of the menin inhibitor that is administered is about 320 mg/day. In some embodiments, the amount of the menin inhibitor that is administered is about 330 mg/day. In some embodiments, the amount of the menin inhibitor that is administered is about 340 mg/day. In some embodiments, the amount of the menin inhibitor that is administered is about 350 mg/day. In some embodiments, the amount of the menin inhibitor that is administered is about 360 mg/day. In some embodiments, the amount of the menin inhibitor that is administered is about 370 mg/day. In some embodiments, the amount of the menin inhibitor that is administered is about 380 mg/day. In some embodiments, the amount of the menin inhibitor that is administered is about 390 mg/day. In some embodiments, the amount of the menin inhibitor that is administered is about 400 mg/day. In some embodiments, the amount of the menin inhibitor that is administered is about 450 mg/day. In some embodiments, the amount of the menin inhibitor that is administered is about 500 mg/day. In some embodiments, the amount of the menin inhibitor that is administered is about 550 mg/day. In some embodiments, the amount of the menin inhibitor that is administered is about 560 mg/day. In some embodiments, the daily dosage is divided into multiple administrations and is given once a day, given twice a day, given three times per day, given four times per day. In some embodiments, the menin inhibitor is administered once per day, twice per day, three times per day.

In some embodiments, the menin inhibitor is administered once per day. In some embodiments, the menin inhibitor is administered twice per day.

In some embodiments, the menin inhibitor is administered at 50 mg QD, 113 mg QD, 113 mg g12 h, 226 mg g12 h, 339 mg g12 h, 452 mg g12 h, or 565 mg g12 h. In some embodiments, the menin inhibitor is a compound of Formula II and is administered at 50 mg QD, 113 mg QD, 113 mg g12 h, 226 mg g12 h, 339 mg g12 h, 452 mg g12 h, or 565 mg g12 h. In some embodiments, the menin inhibitor is a pharmaceutical formulation comprising a compound of Formula II and is administered at 50 mg QD, 113 mg QD, 113 mg g12 h, 226 mg g12 h, 339 mg g12 h, 452 mg g12 h, or 565 mg g12 h. In some embodiments, the menin inhibitor is a capsule comprising a compound of Formula II and is administered at 50 mg QD, 113 mg QD, 113 mg g12 h, 226 mg g12 h, 339 mg g12 h, 452 mg g12 h, or 565 mg g12 h.

In some embodiments, the daily dose of the CYP3A4 inhibitor that is administered in combination with a menin inhibitor is from 50 mg/day up to, and including, 1000 mg/day. In some embodiments, each dose is given once a day, given twice a day, given three times per day, given four times per day. In some embodiments, the CYP3A4 dosage is dependent on the specific CYP3A4 inhibitor. In some embodiments, the daily dosage of each CYP3A4 inhibitor is administered according to approved labeling for other indications. In some embodiments, the amount of the CYP3A4 inhibitor that is administered is about 40 mg/day. In some embodiments, the amount of the CYP3A4 inhibitor that is administered is about 50 mg/day. In some embodiments, the amount of the CYP3A4 inhibitor that is administered is about 60 mg/day. In some embodiments, the amount of the CYP3A4 inhibitor that is administered is about 70 mg/day. In some embodiments, the amount of the CYP3A4 inhibitor that is administered is about 80 mg/day. In some embodiments, the amount of the CYP3A4 inhibitor that is administered is about 90 mg/day. In some embodiments, the amount of the CYP3A4 inhibitor that is administered is about 100 mg/day. In some embodiments, the amount of the CYP3A4 inhibitor that is administered is about 110 mg/day. In some embodiments, the amount of the CYP3A4 inhibitor that is administered is about 120 mg/day. In some embodiments, the amount of the CYP3A4 inhibitor that is administered is about 130 mg/day. In some embodiments, the amount of the CYP3A4 inhibitor that is administered is about 140 mg/day. In some embodiments, the amount of the CYP3A4 inhibitor that is administered is about 150 mg/day. In some embodiments, the amount of the CYP3A4 inhibitor that is administered is about 160 mg/day. In some embodiments, the amount of the CYP3A4 inhibitor that is administered is about 170 mg/day. In some embodiments, the amount of the CYP3A4 inhibitor that is administered is about 180 mg/day. In some embodiments, the amount of the CYP3A4 inhibitor that is administered is about 190 mg/day. In some embodiments, the amount of the CYP3A4 inhibitor that is administered is about 200 mg/day. In some embodiments, the amount of the CYP3A4 inhibitor that is administered is about 210 mg/day. In some embodiments, the amount of the CYP3A4 inhibitor that is administered is about 220 mg/day. In some embodiments, the amount of the CYP3A4 inhibitor that is administered is about 230 mg/day. In some embodiments, the amount of the CYP3A4 inhibitor that is administered is about 240 mg/day. In some embodiments, the amount of the CYP3A4 inhibitor that is administered is about 250 mg/day. In some embodiments, the amount of the CYP3A4 inhibitor that is administered is about 260 mg/day. In some embodiments, the amount of the CYP3A4 inhibitor that is administered is about 270 mg/day. In some embodiments, the amount of the CYP3A4 inhibitor that is administered is about 280 mg/day. In some embodiments, the amount of the CYP3A4 inhibitor that is administered is about 290 mg/day. In some embodiments, the amount of the CYP3A4 inhibitor that is administered is about 300 mg/day. In some embodiments, the amount of the CYP3A4 inhibitor that is administered is about 310 mg/day. In some embodiments, the amount of the CYP3A4 inhibitor that is administered is about 320 mg/day. In some embodiments, the amount of the CYP3A4 inhibitor that is administered is about 330 mg/day. In some embodiments, the amount of the CYP3A4 inhibitor that is administered is about 340 mg/day. In some embodiments, the amount of the CYP3A4 inhibitor that is administered is about 350 mg/day. In some embodiments, the amount of the CYP3A4 inhibitor that is administered is about 360 mg/day. In some embodiments, the amount of the CYP3A4 inhibitor that is administered is about 370 mg/day. In some embodiments, the amount of the CYP3A4 inhibitor that is administered is about 380 mg/day. In some embodiments, the amount of the CYP3A4 inhibitor that is administered is about 390 mg/day. In some embodiments, the amount of the CYP3A4 inhibitor that is administered is about 400 mg/day. In some embodiments, each dose is given once a day, given twice a day, given three times per day, given four times per day.

In some embodiments, the $AUC_{0-24}$ of the menin inhibitor co-administered with a CYP3A4 inhibitor is between about 50 and about 10000 ng*h/mL. In some embodiments, the $C_{max}$ of the menin inhibitor co-administered with a CYP3A4 inhibitor is between about 5 ng/mL and about 1000 ng/mL.

In some embodiments, the CYP3A4 inhibitor is posaconazole and the menin inhibitor is a compound of Formula II. In some embodiments, the CYP3A4 inhibitor is posaconazole which is administered in combination with a pharmaceutical composition comprising a compound of Formula II. In some embodiments, the CYP3A4 inhibitor is a pharmaceutical composition comprising posaconazole which is administered in combination with a pharmaceutical composition comprising a compound of Formula II. In some embodiments, the posaconazole is administered at a 100 mg daily dose, a 200 mg daily dose a 300 mg daily dose, a 400 mg daily dose, or an 800 mg daily dose. In some embodiments, the posaconazole is administered as an injection 300 mg once daily. In some embodiments, the CYP3A4 inhibitor is posaconazole administered as a 300 mg injection twice daily followed by a 300 mg injection once daily. In some embodiments, the CYP3A4 inhibitor is posaconazole and the posaconazole is administered as a 300 mg tablet once daily. In some embodiments, the CYP3A4 inhibitor is posaconazole and the posaconazole is administered at 2× the daily dose on the first day of treatment. In some embodiments, the posaconazole is administered as an oral suspension. In some embodiments, the daily dosage of the posaconazole oral suspension is 100 mg. In some embodiments, the CYP3A4 inhibitor is posaconazole and the posaconazole is administered at 2× the daily dose on the first day of treatment. In some embodiments, the posaconazole is administered as an oral suspension. In some embodiments, the daily dosage of the posaconazole oral suspension is 800 mg. In some embodiments, the daily dosage of the posaconazole oral suspension is 800 mg divided as two 400 mg administrations twice a day.

In some embodiments, the CYP3A4 inhibitor is ritonavir. In some embodiments, the ritonavir is administered at 1200 mg daily. In some embodiments, the ritonavir is administered at 600 mg twice daily. In some embodiments, the ritonavir is administered at 300 mg twice daily and increased at 2 to 3-day intervals by 100 mg twice daily.

In some embodiments, the CYP3A4 inhibitor is cobicistat. In some embodiments, the cobicistat is administered in a pharmaceutical composition. In some embodiments, the cobicistat pharmaceutical composition is a tablet. In some embodiments, the cobicistat daily dose is 150 mg. In some embodiments, the cobicistat is administered once daily at 150 mg.

In some embodiments, the CYP3A4 inhibitor is administered once per day, twice per day, or three times per day. In some embodiments, the CYP3A4 inhibitor is administered once per day. In some embodiments, the CYP3A4 inhibitor is administered once per day, twice per day, three times per day, four times per day. In some embodiments, the CYP3A4 inhibitor is administered once per day. In some embodiments, the menin inhibitor and the CYP3A4 inhibitor are co-administered (e.g., in a single dosage form or in separate dosage forms), once per day. In some embodiments, the menin inhibitor is administered twice per day and the CYP3A4 inhibitor is administered (e.g., in a single dosage form or in separate dosage forms), four times per day. In some embodiments, the menin inhibitor is administered twice per day and the CYP3A4 inhibitor is administered (e.g., in a single dosage form or in separate dosage forms), twice per day. In some embodiments, the menin inhibitor and the CYP3A4 inhibitor are maintenance therapy. In some embodiments, the menin inhibitor is maintenance therapy.

In some embodiments, the compositions disclosed herein are administered for prophylactic, therapeutic, or maintenance treatment. In some embodiments, the compositions disclosed herein are administered for therapeutic applications. In some embodiments, the compositions disclosed herein are administered as a maintenance therapy, for example for a patient in remission.

In the case wherein the patient's status does not improve, the administration of the compounds may be given continuously; alternatively, the dose of drug being administered may be increased for a certain length of time. The length of the drug increase can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose increase may be from 10%-200%, including, by way of example only, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200%.

If improvement of the patient's conditions has not occurred, the dosage or the frequency of administration, or both, can be increased, as a function of the symptoms, to a level at which the improved disease, disorder or condition is achieved.

In the case wherein the patient's status does improve, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers.

Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In some embodiments, the menin inhibitor and the menin inhibitor are administered concurrently. In some embodiments, the menin inhibitor and the CYP3A4 inhibitor are administered simultaneously, essentially simultaneously or within the same treatment protocol. In some embodiments, the menin inhibitor and the CYP3A4 inhibitor are administered sequentially.

In some embodiments, the menin inhibitor and the CYP3A4 inhibitor are administered concurrently. In some embodiments, the menin inhibitor and the CYP3A4 inhibitor are administered simultaneously, essentially simultaneously or within the same treatment protocol. In some embodiments, the menin inhibitor and the CYP3A4 inhibitor are administered sequentially.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include the CYP3A4 inhibitor, optionally in a composition or in combination with a CYP3A4 inhibitor as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In some embodiments, the pack or dispenser device is accompanied by instructions for administration. In some embodiments, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are also prepared, placed in an appropriate container, and labeled for treatment of an indicated condition.

| Abbreviation | Definition |
|---|---|
| ALL | Acute lymphoblastic leukemia |
| ALT | Alanine aminotransferase |

-continued

| Abbreviation | Definition |
|---|---|
| AML | Acute myeloid leukemia |
| $AUC_{0-24}$ | Area under the plasma concentration curve from time 0 to 24 hours |
| $AUC_{0-t}$ | area under the concentration versus time curve from time 0 to t |
| C | Cycle |
| CL/F | Apparent oral clearance |
| $C_{max}$ | Maximum plasma concentration |
| CR | Complete remission |
| CRc | Composite definition of complete remission |
| CRh | Complete remission with partial hematologic recovery |
| CRi | Complete remission with incomplete hematologic recovery |
| CRp | Complete remission with incomplete platelet recovery |
| CYP | Cytochrome P450 |
| D | Day |
| DLT | Dose-limiting toxicity |
| DNA | Deoxyribonucleic acid |
| DOR | Duration of response |
| EF | Ejection fraction |
| FISH | Fluorescence in situ hybridization |
| GFR | Glomerular filtration rate |
| GVHD | Graft-versus-host disease |
| HDL | High-density lipoprotein |
| HEENT | Head/ears/eyes/nose/throat |
| HGB | Hemoglobin |
| HSC | Hematopoietic stem cell |
| HSCT | Hematopoietic stem cell transplant |
| $IC_{50}$ | 50% inhibitory concentration |
| $K_i$ | Inhibitory constant |
| | Lysine (K) methyltransferase 2A |
| MLL1 | Mixed lineage leukemia 1 gene |
| MLLr | Mixed lineage leukemia-rearranged |
| MPAL | Mixed phenotype acute leukemia |
| NPM1 | Nucleophosmin 1 |
| NPM1c | Nucleophosmin 1 mutation |
| OS | Overall survival |
| PBMC | Peripheral blood mononuclear cell |
| PCR | Polymerase chain reaction |
| PD | Progressive disease |
| PK | Pharmacokinetic |
| PO | Oral(ly) |
| PR | Partial remission |
| q12h | Every 12 hours |
| QD | Once daily |
| QTc | Corrected QT interval |
| QTcF | Corrected QT interval by Fredericia |
| R/R | Relapsed/refractory |
| RBC | Red blood cell count |
| RFS | Relapse-free survival |
| RNA | Ribonucleic acid |
| $t_{1/2}$ | Half-life |
| $T_{max}$ | Time to maximum plasma concentration |
| TTR | Time to response |
| ULN | Upper limit of normal |
| Vz/F | Apparent volume of distribution |
| WBC | White blood cell count |
| wt | Wild type |

EXAMPLES

The following ingredients, formulations, processes and procedures for practicing the methods disclosed herein correspond to that described above and are not meant to be limiting to the aforementioned embodiments.

Example 1: Treatment with Menin Inhibitor of Formula I or Formula II Alone and in Combination with a CYP3A4 Inhibitor Patients aged ≥12 years with R/R acute leukemia for whom there is no available therapy are enrolled. The menin inhibitor is dosed on an every 12 hour (q12 h) schedule; alternative dose schedules are considered. The menin inhibitor is administered orally (PO) in 28-day cycles, with the first dose administered on Cycle 1, Day 1 (C1D1). Patients continue treatment until progressive disease (PD) or unacceptable toxicity.

Patients are assigned to one of two arms as described below:

Arm A: Patients must not be receiving any strong cytochrome P450 3A4 (CYP3A4) inhibitor/inducers. Patients who were receiving a strong CYP3A4 inhibitor/inducer must have discontinued the medication at least 7 days prior to enrollment.

Arm B: Patients must be receiving itraconazole, ketoconazole, posaconazole, or voriconazole (strong CYP3A4 inhibitors) for antifungal prophylaxis for at least 7 days prior to enrollment and while on treatment. Patients must not be receiving any other strong CYP3A4 inhibitors/inducers.

The dosage of the menin inhibitor in patients with acute leukemia is determined Patients with R/R acute leukemia are enrolled agnostic of genetic mutation status. The exact dose strengths have been rounded down to accommodate capsule size constraint (113 mg/capsule). The starting dose will be 113 mg g12 h, with escalation to higher doses or de-escalation to lower doses as shown in the table below.

Dose Levels of Menin Inhibitor

| Dose Level | Proposed Dose Increment (%) | Dose |
|---|---|---|
| −2 | −50% of Dose Level −1 | 50 mg QD |
| −1 | −50% of Dose Level 1 | 113 mg QD |
| 1 | Starting Dose | 113 mg q12h |
| 2 | 100% | 226 mg q12h |
| 3 | 50% | 339 mg q12h |
| 4 | 33% | 452 mg q12h |
| 5 | 25% | 565 mg q12h |

Efficacy of the menin inhibitor and the combination therapy is explored in 3 indication-specific cohorts, as follows:

Cohort 2A: Patients with MLLr ALL/MPAL.

Cohort 2B: Patients with MLLr AML.

Cohort 2C: Patients with NPM1c AML.

Each Cohort employs a Simon 2-stage design with up to 34 patients in each cohort. Enrollment in each Expansion Cohort is conducted independently. A CR+CRh rate >15% is considered the lower bound for anti-leukemic activity in patients with R/R acute leukemia harboring either NPM1c or MLL gene rearrangement and who have no available therapeutic options.

The anti-tumor activity of the menin inhibitor is evaluated in genetically defined cohorts. These patient sub-populations have leukemias that express the target for which the menin inhibitor is predicted to be most efficacious.

The dose is based upon the data generated from the rat and dog 28-day GLP toxicology studies. The starting dose is set as the human equivalent dose of the lower of either 1/10 of the STD10 in rats or 1/6 the HNSTD in dogs. The HNSTD in dog (50 mg/kg; 1000 mg/m$^2$) was lower than STD10 in rats (400 mg/kg; 2400 mg/m$^2$); therefore, the clinical starting dose is 1/6 HNSTD in dog or 166.7 mg/m$^2$, equating to a dose of 4.5 mg/kg in adults. A total daily dose of 225 mg of the menin inhibitor was selected as the starting dose, which rounded to the nearest capsule size, is 226 mg per day. The dose is administered as 113 mg PO g12 h.

The safety, tolerability, MTD, and RP2D of the menin inhibitor and combination therapy in patients with R/R acute leukemia is determined in Arm A and Arm B, respectively. The PK parameters of the menin inhibitor and combination therapy in Arm A and Arm B, respectively are determined. The short- and long-term safety and tolerability of the menin inhibitor and combination therapy is determined. The CR rate (CR+CRh) is determined.

Secondary Objectives are Determined:

the composite CR (CRc) rate (CR+CRh+CR with incomplete hematologic recovery [CRi]+CR with incomplete platelet recovery [CRp]).

the CR rate after 4 weeks of therapy.

the best overall remission rate (BORR) (CRc+ partial remission [PR]).

the relapse-free survival (RFS).

the time to response (TTR) and duration of response (DOR)

the overall survival (OS).

the PK parameters of the menin inhibitor and combination therapy $C_{max}$, $T_{max}$, $AUC_{0-t}$, $AUC_{0-24}$, CL/F, Vz/F and $t_{1/2}$.

The anti-leukemic activity of the menin inhibitor and combinations of the present invention is determined. The menin inhibitor and combinations of the current invention pharmacodynamic, safety and efficacy relationship with correlative biomarkers, which may include immunophenotyping of circulating peripheral blood mononuclear cells (PBMC) and/or bone marrow, gene expression, mutational analysis and minimal residual disease (MRD).

Documented R/R Acute Leukemia.

Arm A: Patients must not be receiving any strong cytochrome P450 3A4 (CYP3A4) inhibitor/inducers. Patients who were receiving a strong CYP3A4 inhibitor/inducer must have discontinued the medication at least 7 days prior to enrollment.

Arm B: Patients must be receiving itraconazole, ketoconazole, posaconazole, or voriconazole (strong CYP3A4 inhibitors) for antifungal prophylaxis for at least 7 days prior to enrollment and while on treatment with the menin inhibitor. Patients must not be receiving any other strong CYP3A4 inhibitors/inducers.

Cohort 2A: Documented R/R ALL/MPAL with an MLLr translocation.

Cohort 2B: Documented R/R AML with an MLLr translocation.

Cohort 2C: Documented R/R AML with NPM1c.

Central confirmation of MLLr status is obtained by fluorescence in situ hybridization (11q23 MLL-Break Apart FISH) testing (Cancer Genetics Inc., Rutherford, NJ). Central confirmation of NPM1 mutational status is obtained by NPM1 (nucleophosmin) gene analysis, exon 12 variants (CPT 81310) (Cancer Genetics, Inc., Rutherford, NJ). Patients whose mutational status cannot be confirmed centrally are replaced.

Recurrent or refractory AML/ALL or MPAL, as defined by standardized criteria (eg, European LeukemiaNet criteria; International Working Group criteria) after standard of care therapy. Patients with persistent leukemia after initial therapy or with recurrence of leukemia at any time after achieving a response during or after the course of treatment (including allogeneic hematopoietic stem cell transplant [HSCT]) are eligible.

Prior Therapy:

Any prior treatment-related toxicities resolved to ≤Grade 1 prior to enrollment, with the exception of ≤Grade 2 neuropathy or alopecia.

Radiation Therapy: At least 60 days from prior total body irradiation (TBI), craniospinal radiation and/or ≥50% radiation of the pelvis, or at least 14 days from local palliative radiation therapy (small port).

Stem Cell Infusion: At least 60 days must have elapsed from HSCT and at least 4 weeks (from first dose) must have elapsed from donor lymphocyte infusion (DLI) without conditioning.

Immunotherapy: At least 42 days since prior immunotherapy, including tumor vaccines and checkpoint inhibitors, and at least 21 days since receipt of chimeric antigen receptor therapy or other modified T cell therapy.

Anti-Leukemia Therapy: At least 14 days since the completion of anti-leukemic therapy (for example, but not limited to, small molecule or cytotoxic/myelosuppressive therapy), with the following exceptions: Hydroxyurea for cytoreduction can be initiated and continued concomitantly with the menin inhibitor, with medical monitor approval. Intrathecal chemotherapy at the time of diagnostic lumbar puncture at least 24 hours prior to the start of the menin inhibitor. Patients are permitted to receive intrathecal chemotherapy.

Hematopoietic Growth Factors: At least 7 days since the completion of therapy with short-acting hematopoietic growth factors and 14 days with long-acting growth factors.

Biologics (eg monoclonal antibody therapy): At least 7 days or 5 half-lives, whichever is longer, since the completion of therapy with a biologic agent.

Steroids: At least 7 days since systemic glucocorticoid therapy, unless receiving physiologic dosing (equivalent to ≤10 mg prednisone daily) or cytoreductive therapy. Cytoreductive therapy must have approval of the medical monitor.

Menin Inhibitor Administration

Menin inhibitor capsules (113 and 156 mg free base equivalents) for PO administration is taken g12 h at the designated dose according to patients' cohort assignment. The menin inhibitor is administered on an empty stomach, at least 2 hours after a meal and 1 hour before the next meal. All patients receive menin inhibitor PO g12 h in 28-day cycles, with the first study drug dose administered on C1D1. Alternative dosing schedules are possible based on the dosing table above. Patients continue dosing until development of PD or unacceptable toxicity.

Dose Assignment: Phase 1

The starting dose of the menin inhibitor is 113 mg g12 h (226 mg total daily dose). The menin inhibitor doses are escalated along with the CYP3A4 dosage.

The doses are determined independently for Arm A and Arm B that meet the following criteria:

- ≤⅙ of DLT-evaluable patients experience a DLT.
- At least two-thirds of patients received at least 80% of their prescribed doses in C1 and C2, unless due to PD.
- At least 3 patients are evaluable for PK.
- At least two-thirds of patients have area under the plasma concentration curve from time 0 to 24 hours ($AUC_{0-24}$) values ≥15,000 ng·hr/mL.
  - If the MTD does not achieve this exposure level, but efficacy is seen in any dose level, then the highest dose level that meets the above safety and tolerability criteria will be selected as the RP2D If the highest tested dose does not meet all 4 RP2D criteria, then the next lower dose level will be expanded to a total of 6 patients. Expansion of lower dose levels will continue in a sequential fashion until identification of a dose meeting the RP2D criteria. Additionally, observations related to PK and any cumulative toxicity observed after multiple cycles may be included in the rationale supporting the RP2D.

If a 100% CR rate is observed at the end of Cycle I in a dose level that is safe and tolerable as 5 defined above during the 3+3 dose escalation period, then that dose will be defined as the RP2D.

Efficacy

Disease assessments are performed and disease response assessed.

- Complete remission (CR): Bone marrow blasts <5%; absence of circulating blasts and blasts with Auer rods; absence of extramedullary disease; ANC ≥$1.0\times10^9$/µL (1000/µL) and platelet count ≥$100\times10^9$/µL (100 000/µL)
- CR with partial hematologic recovery (CRh): Bone marrow blasts <5%; absence of circulating blasts and blasts with Auer rods; absence of extramedullary disease; residual neutropenia (>$0.5\times10^9$/µL [1000/µL]) and thrombocytopenia (>$50\times10^9$/µL [100 000/µL])
- CR with incomplete hematologic recovery (CRi): Bone marrow blasts <5%; absence of circulating blasts and blasts with Auer rods; absence of extramedullary disease; residual neutropenia (<$1.0\times10^9$/µL [1000/µL]) or thrombocytopenia (<$100\times10^9$/µL [100 000/µL])
- CR with incomplete platelet recovery (CRp): Bone marrow blasts <5%; absence of circulating blasts and blasts with Auer rods; absence of extramedullary disease; ANC ≥$1.0\times10^9$/µL (1000/µL) and platelet count <$100\times10^9$/µL (100 000/µL).
- Partial remission (PR): decrease of bone marrow blast percentage to 5% to 25%; and decrease of pretreatment bone marrow blast percentage by at least 50%; ANC ≥$1.0\times10^9$/L (1000/µL) and platelet count ≥$100\times10^9$/µL (100 000/µL).

Pharmacokinetics

Blood samples of approximately 5 mL each will be collected for measurement of plasma concentrations of the menin inhibitor. A maximum of 24 additional samples may be collected at other time points during the study.

Blood samples for PK are collected on C1D1, C1D8, C3D1, and C5D1 at predose (within 1 hour prior to dosing) and at 0.25, 0.5, and 1 hour (±5 minutes), 2 and 4 hours (±15 minutes), and 8 hours (±30 minutes) postdose and centrifuged to prepare plasma. For Arm B only, a PK sample is also to be collected on C1D3 or 4 at predose (within 1 hour prior to dosing). On PK sample collection days, the menin inhibitor is to be taken at the study center under the observation of study center personnel.

Statistical Considerations

Statistical Hypotheses

The study uses a Simon minimax 2-stage design. A true CR+CRh rate of 35% is hypothesized. The CR+CRh rate >15% is considered the lower bound for anti-leukemic activity in patients with relapsed and refractory acute leukemia.

21 patients are enrolled in each cohort. If 4 or more patients experience a response in a single cohort, then an additional 13 patients will be enrolled in that cohort. If 10 or more patients with CR+CRh are observed among the 34 patients in a cohort, then the treatment is worthy of further evaluation.

Sample Size Determination

The actual number of patients to be enrolled in Phase 1 is dependent on the dose level(s) at which toxicities are seen and the number of dose levels investigated to identify the MTD and RP2D. It is anticipated that up to 54 patients will be enrolled in Phase 1, with up to 30 patients in Arm A and up to 24 patients in Arm B. No formal sample size calculation was performed for Phase 1 of the study.

The number of patients in each cohort evaluated in each stage and the minimum number of responders needed to continue to the next stage, is determined based on the minimax version of Simon's 2-stage design, with 80% power and 1-sided significance level of 2.5%. A maximum of 34 patients will be enrolled in each cohort. A true CR+CRh rate of 35% is hypothesized. A CR+CRh rate greater than 15% is considered the lower threshold for antileukemic activity. Based on the design elements specified above, up to 21 patients will be enrolled in each cohort during the first stage: If 4 or more patients achieve CR+CRh, 13 additional patients will be enrolled during second stage. Otherwise, enrollment will be terminated for that cohort. Upon completion of the second stage, if 10 or more patients out of 34 enrolled patients in a cohort achieve CR+CRh, further evaluation may be pursued for that patient population. If the true CR+CRh rate is 15% or less for a leukemic subtype, the probability of terminating enrollment at the end of the first stage is 61%. Therefore, it is anticipated that up to 156 patients are to be enrolled and treated with menin inhibitors of Formula I or Formula II in combination with a CYP3A4 inhibitor in this study.

Analyses

For purposes of analysis, the following populations are defined:

| Population | Description |
|---|---|
| Intention-to-treat (ITT) | All patients enrolled who provide informed consent. |
| DLT | All patients with data used for implementing the dose-escalation schedule. These patients will have received 75% of all study drug doses in C1 (ie, the DLT evaluation period) or stopped treatment because of DLTs in the DLT evaluation period. |
| Evaluable | All patients who received at least one dose of study drug and centrally confirmed for mutational status. |
| Safety | Consists of all enrolled patients who received at least one dose of study drug during the study. |
| PK | All patients who receive at least one dose of the menin inhibitors of Formula I or Formula II in combination with a CYP3A4 inhibitor and have at least one valid plasma concentration of menin inhibitors of Formula I or Formula II and or CYP3A4 inhibitor determined. |
| Pharmacodynamic | Patients who are exposed to menin inhibitors of Formula I or Formula II in combination with a CYP3A4 inhibitor and have sufficient samples collected to permit pharmacodynamic analyses. |

Statistical Analyses

Detailed methodology for summary and statistical analyses of the data collected in this study will be documented in a statistical analysis plan (SAP). The SAP will be finalized before database lock and will describe the analysis populations to be included in the analyses, and procedures for accounting for missing, unused and spurious data. This section is a summary of the planned statistical analyses of the primary and secondary endpoints. The statistical analyses of the exploratory endpoints. Time-to-event data will be analyzed using the Kaplan-Meier method and results will be summarized by 25th, 50th (median) and 75th percentiles with associated 2-sided 95% CIs, as well as the percentage of censored observations.

The statistical analyses are performed using SAS© version 9.4 or later (SAS Institute Inc, Cary NC). Programming specifications are prepared that describe the datasets and variables created for this study. The datasets are prepared using the most recent version of CDISC's Study Data Tabulation Model (SDTM) and Analysis Dataset Model (ADaM).

Pharmacokinetic Analyses

Plasma concentrations of the administered menin inhibitor are determined with a validated bioanalytical assay. The following PK parameters are calculated from plasma concentrations determined on C1D1, C1D8, C3D1 and C5D1, if appropriate: $C_{max}$, $T_{max}$, $AUC_{0-t}$, $AUC_{0-24}$, CL/F, Vz/F and $t_{1/2}$ by conventional non-compartmental analysis when sufficient data are available. The concentration at 12 h after the morning dose (predose for evening dose) is imputed with the concentration in the sample collected before the morning dose (predose for morning dose), as the values should be similar. $AUC_{0-24}$ at steady state may be calculated as two times $AUC_{0-12}$ with g12 h dosing.

Summary statistics for plasma concentrations and pharmacokinetic parameters are generated by dose cohort and across cohorts.

Other Analyses

Pharmacodynamic, and biomarker exploratory analyses will be described in the statistical analysis plan finalized before database lock.

Strong Inhibitors and Inducers of CYP3A4 and CYP3A Substrates with Narrow Therapeutic Range

| | |
|---|---|
| Strong inhibitors of CYP3A4[a] | |
| boceprevir | nefazodone |
| clarithromycin | nelfinavir |
| conivaptan | posaconazole |
| grapefruit juice | ritonavir |
| indinavir | saquinavir |
| itraconazole | telaprevir |
| ketoconazole | telithromycin |
| lopinavir | voriconazole |
| mibefradil | |
| Strong Inducers of CYP3A4[b] | |
| avasimibe | phenytoin |
| carbamazepine | rifampin |
| enzalutamide | St John's wort |
| Examples of CYP3A Substrates with Narrow Therapeutic Range[c] | |
| alfentanil | pimozide |
| cisapride | quinidine |
| cyclosporine | sirolimus |
| dihydroergotamine | tacrolimus |
| ergotamine | terfenadine |
| fentanyl | |

Abbreviations: AUC-area under the concentration versus time curve; CYP3A4-cytochrome P450 3A4.

[a]Increases the AUC of the substrate by ≥5-fold

[b]Decreases the AUC of the substrate by ≥80%

[c]Refers to drugs whose exposure-response relationship indicates that small increases in their exposure levels by the concomitant use of CYP inhibitors may lead to serious safety concerns (eg, Torsades de Pointes)

Note: The above lists are not exhaustive. See also:

http://www.fda.gov/drugs/developmentapprovalprocess/developmentresources/druginteractionslabeling/ucm093664.htm

EQUIVALENTS

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

The invention claimed is:

1. A method of treating a leukemia in a human in need thereof comprising orally administering about 280-350 mg/day of a menin inhibitor of Formula (II), Formula (II)

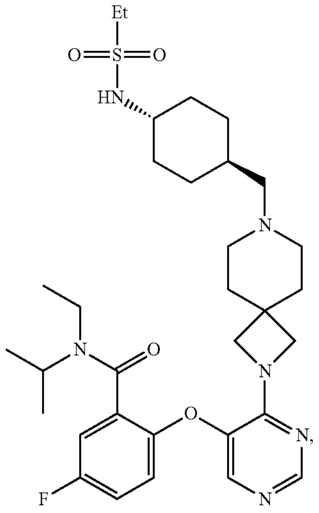

and a strong CYP3A4 inhibitor.

2. The method of claim 1, wherein the strong CYP3A4 inhibitor is selected from the group consisting of boceprevir, nefazodone, clarithromycin, nelfinavir, conivaptan, posaconazole, grapefruit juice, ritonavir, indinavir, saquinavir, itraconazole, telaprevir, ketoconazole, telithromycin, lopinavir, voriconazole, cobicistat, and mibefradil.

3. The method of claim 1, wherein the strong CYP3A4 inhibitor is an azole antifungal.

4. The method of claim 1, wherein the menin inhibitor and the strong CYP3A4 inhibitor are in separate unit doses.

5. The method of claim 1, wherein the menin inhibitor and the strong CYP3A4 inhibitor are administered concurrently, sequentially, simultaneously, essentially simultaneously or within a treatment protocol.

6. The method of claim 1, comprising administering about 300-340 mg/day of the menin inhibitor of Formula (II).

7. The method of claim 6, comprising administering about 310 mg/day of the menin inhibitor of Formula (II).

8. The method of claim 6, comprising administering about 320 mg/day of the menin inhibitor of Formula (II).

9. The method of claim 6, comprising administering about 330 mg/day of the menin inhibitor of Formula (II).

10. The method of claim 1, wherein the 280-350 mg/day dosage is divided into multiple doses which are administered twice daily.

11. The method of claim 10, wherein the 320 mg/day dosage is divided into multiple doses which are administered twice daily.

12. The method of claim 1, wherein the leukemia is mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL), acute myeloid leukemia (AML), acute granulocytic leukemia, acute nonlymphocytic leukemia, chronic lymphocytic leukemia (CLL), chronic myelogenous leukemia (CML), therapy related leukemia, myelodysplastic syndrome (MDS), myeloproliferative disease (MPD), myeloproliferative neoplasia (MPN), plasma cell neoplasm, multiple myeloma, myelodysplasia, cutaneous T-cell lymphoma, lymphoid neoplasm, AIDS-related lymphoma, thymoma, thymic carcinoma, mycosis fungoides, Alibert-Bazin syndrome, granuloma fungoides, Sezary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non-Hodgkin's lymphoma (malignant lymphoma), or Waldenstrom's macroglobulinemia.

13. The method of claim 1, wherein the leukemia is an acute leukemia.

14. The method of claim 1, wherein the leukemia is AML or ALL.

15. The method of claim 1, wherein the leukemia is a MLL-r leukemia.

16. The method of claim 1, wherein the leukemia is a nucleophosmin (NPM1)-mutated leukemia.

17. The method of claim 1, wherein the CYP3A4 inhibitor is selected from the group consisting of cobicistat, posaconazole, itraconazole, and voriconazole.

18. The method of claim 1, wherein the menin inhibitor of Formula (II) is administered as a pharmaceutically acceptable salt, solvate, and/or hydrate thereof.

19. A method of treating an NPM1-mutated leukemia or a MLL-r leukemia in a human in need thereof comprising orally administering about 320 mg/day of a menin inhibitor of Formula (II), Formula (II)

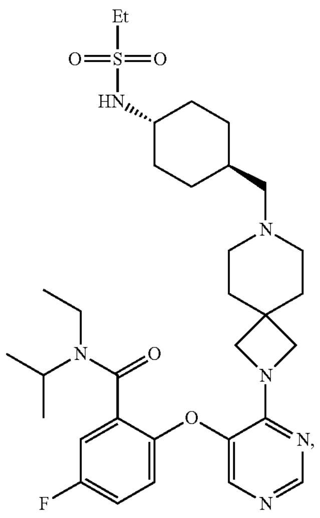

wherein the menin inhibitor of Formula (II) is administered twice daily, and a strong CYP3A4 inhibitor.

20. The method of claim 19, wherein the strong CYP3A4 inhibitor is selected from the group consisting of boceprevir, nefazodone, clarithromycin, nelfinavir, conivaptan, posaconazole, grapefruit juice, ritonavir, indinavir, saquinavir, itraconazole, telaprevir, ketoconazole, telithromycin, lopinavir, voriconazole, cobicistat, and mibefradil.

21. The method of claim 19, wherein the strong CYP3A4 inhibitor is selected from the group consisting of cobicistat, posaconazole, itraconazole, and voriconazole.

22. The method of claim 19, wherein the strong CYP3A4 inhibitor is an azole antifungal.

23. The method of claim 19, wherein the menin inhibitor and the CYP3A4 inhibitor are in separate unit doses.

24. The method of claim 19, wherein the menin inhibitor and the strong CYP3A4 inhibitor are administered simultaneously.

25. The method of claim 19, wherein the menin inhibitor of Formula (II) is administered as a pharmaceutically acceptable salt, solvate, and/or hydrate thereof.

26. A method of treating an ALL or AML in a human in need thereof comprising orally administering about 320 mg/day of a menin inhibitor of Formula (II),

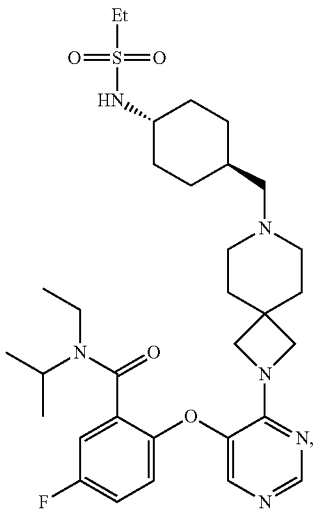

Formula (II)

and a strong CYP3A4 inhibitor.

27. The method of claim 26, wherein the strong CYP3A4 inhibitor is selected from the group consisting of boceprevir, nefazodone, clarithromycin, nelfinavir, conivaptan, posaconazole, grapefruit juice, ritonavir, indinavir, saquinavir, itraconazole, telaprevir, ketoconazole, telithromycin, lopinavir, voriconazole, cobicistat, and mibefradil.

28. The method of claim 26, wherein the strong CYP3A4 inhibitor is an azole antifungal.

29. The method of claim 26, wherein the menin inhibitor and the strong CYP3A4 inhibitor are in separate unit doses.

30. The method of claim 26, wherein the menin inhibitor of Formula (II) and the strong CYP3A4 inhibitor are administered concurrently, sequentially, simultaneously, essentially simultaneously or within the same treatment protocol.

31. The method of claim 26, wherein the 320 mg/day dosage of Formula (II) is divided into multiple doses which are administered twice daily.

32. The method of claim 26, wherein the strong CYP3A4 inhibitor is selected from the group consisting of cobicistat, posaconazole, itraconazole, and voriconazole.

* * * * *